United States Patent
Lee et al.

(10) Patent No.: US 9,416,379 B2
(45) Date of Patent: Aug. 16, 2016

(54) MUTANT MICROORGANISM HAVING IMPROVED 1,4-BDO PRODUCTIVITY AND METHOD OF PREPARING 1,4-BDO USING THE MUTANT MICROORGANISM

(71) Applicant: Samsung Electronics Co., Ltd., Suwon-si, Gyeonggi-do (KR)

(72) Inventors: Kyu-sang Lee, Ulsan (KR); Young-min Lee, Suwon-si (KR); Woo-yong Lee, Hwaseong-si (KR); Hyun-min Koo, Seoul (KR); Jin-woo Kim, Seoul (KR); Young-kyoung Park, Seoul (KR); Jin-hwan Park, Suwon-si (KR); Hwa-young Cho, Hwaseong-si (KR); Jae-chan Park, Yongin-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 124 days.

(21) Appl. No.: 13/952,410

(22) Filed: Jul. 26, 2013

(65) Prior Publication Data
US 2014/0030781 A1  Jan. 30, 2014

(30) Foreign Application Priority Data
Jul. 27, 2012 (KR) ........................ 10-2012-0082815

(51) Int. Cl.
*C12N 1/20* (2006.01)
*C12P 7/18* (2006.01)
*C12N 15/77* (2006.01)
*C12N 9/04* (2006.01)
*C12N 15/52* (2006.01)

(52) U.S. Cl.
CPC .................. *C12P 7/18* (2013.01); *C12N 9/0006* (2013.01); *C12N 15/52* (2013.01); *C12N 15/77* (2013.01); *C12Y 101/01037* (2013.01); *C12Y 101/05004* (2013.01); *Y02P 20/52* (2015.11)

(58) Field of Classification Search
CPC .................... C12Y 102/00; C12Y 102/01016; C12P 7/18; C12N 9/0008

USPC ........................................ 435/25, 158, 252.32
See application file for complete search history.

(56) References Cited

U.S. PATENT DOCUMENTS

| 7,214,526 | B2 | 5/2007 | Bathe et al. |
|---|---|---|---|
| 7,858,350 | B2 | 12/2010 | Burk et al. |
| 7,947,483 | B2 | 5/2011 | Burgard et al. |
| 8,067,214 | B2 | 11/2011 | Burk et al. |
| 8,129,169 | B2 * | 3/2012 | Van Dien et al. .......... 435/252.3 |
| 2011/0045575 | A1 | 2/2011 | Van Dien et al. |
| 2011/0159572 | A1 | 6/2011 | Burk et al. |
| 2011/0229946 | A1 | 9/2011 | Haselbeck et al. |
| 2013/0217086 | A1 | 8/2013 | Lee et al. |

FOREIGN PATENT DOCUMENTS

| KR | 2012/0015526 | 2/2000 |
|---|---|---|
| KR | 1020090025902 A | 3/2009 |

OTHER PUBLICATIONS

Kjeldsen et al., "In Silico Genome-Scale Reconstruction and Validation of the *Corynebacterium glutamicum* Metabolic Network," *Biotechnology and Bioengineering*, 102(2): 583-597 (2009).

Shinfuku et al., "Development and experimental verification of a genome-scale metabolic model for *Corynebacterium glutamicum*," *Microbial Cell Factories*, 8(43): 1-15 (2009).

Yim et al., "Metabolic engineering of *Escherichia coli* for direct production of 1,4-butanediol," *Nature Chemical Biology*, 7: 445-452 (2011).

Wendisch et al., Metabolic engineering of *Escherichia coli* and *Corynebacterium glutamicum* for biotechnological production of organic acids and amino acids, *Current Opinion in Microbiology*, 9: 268-274 (2006).

* cited by examiner

*Primary Examiner* — Tekchand Saidha
(74) *Attorney, Agent, or Firm* — Leydig, Voit & Mayer, Ltd.

(57) ABSTRACT

A recombinantly modified *Corynebacterium glutamicum* microorganism with an improved 1,4-butanediol (1,4-BDO) productivity relative to an unmodified *Corynebacterium glutamicum* microorganism, wherein activity of an enzyme catalyzing a conversion reaction between malate and oxaloacetate is inactivated or reduced relative to an unmodified *Corynebacterium glutamicum* microorganism, as well as a method of making and using same.

19 Claims, 3 Drawing Sheets
(1 of 3 Drawing Sheet(s) Filed in Color)

SEQUENCE LISTING

<160> NUMBER OF SEQ ID NOS: 30

<210> SEQ ID NO 1
<211> LENGTH: 371
<212> TYPE: PRT
<213> ORGANISM: Artificial Sequence
<220> FEATURE:
<223> OTHER INFORMATION: Synthetic (4hbD)

<400> SEQUENCE: 1

Met Gln Leu Phe Lys Leu Lys Ser Val Thr His His Phe Asp Thr Phe
1               5                   10                  15

Ala Glu Phe Ala Lys Glu Phe Cys Leu Gly Glu Arg Asp Leu Val Ile
            20                  25                  30

Thr Asn Glu Phe Ile Tyr Glu Pro Tyr Met Lys Ala Cys Gln Leu Pro
        35                  40                  45

Cys His Phe Val Met Gln Glu Lys Tyr Gly Gln Gly Glu Pro Ser Asp
    50                  55                  60

Glu Met Met Asn Asn Ile Leu Ala Asp Ile Arg Asn Ile Gln Phe Asp
65                  70                  75                  80

Arg Val Ile Gly Ile Gly Gly Gly Thr Val Ile Asp Ile Ser Lys Leu
                85                  90                  95

Phe Val Leu Lys Gly Leu Asn Asp Val Leu Asp Ala Phe Asp Arg Lys
            100                 105                 110

Ile Pro Leu Ile Lys Glu Lys Glu Leu Ile Ile Val Pro Thr Thr Cys
        115                 120                 125

Gly Thr Gly Ser Glu Val Thr Asn Ile Ser Ile Ala Glu Ile Lys Ser
    130                 135                 140

Arg His Thr Lys Met Gly Leu Ala Asp Asp Ala Ile Val Ala Asp His
145                 150                 155                 160

Ala Ile Ile Ile Pro Glu Leu Leu Lys Ser Leu Pro Phe His Phe Tyr
                165                 170                 175

Ala Cys Ser Ala Ile Asp Ala Leu Ile His Ala Ile Glu Ser Tyr Val
            180                 185                 190

Ser Pro Lys Ala Ser Pro Tyr Ser Arg Leu Phe Ser Glu Ala Ala Trp
        195                 200                 205

Asp Ile Ile Leu Glu Val Phe Lys Lys Ile Ala Glu His Gly Pro Glu
210                 215                 220

Tyr Arg Phe Glu Lys Leu Gly Glu Met Ile Met Ala Ser Asn Tyr Ala
225                 230                 235                 240

Gly Ile Ala Phe Gly Asn Ala Gly Val Gly Ala Val His Ala Leu Ser
                245                 250                 255

Tyr Pro Leu Gly Gly Asn Tyr His Val Pro His Gly Glu Ala Asn Tyr
            260                 265                 270

Gln Phe Phe Thr Glu Val Phe Lys Val Tyr Gln Lys Lys Asn Pro Phe
        275                 280                 285

Gly Tyr Ile Val Glu Leu Asn Trp Lys Leu Ser Lys Ile Leu Asn Cys
    290                 295                 300

Gln Pro Glu Tyr Val Tyr Pro Lys Leu Asp Glu Leu Leu Gly Cys Leu
305                 310                 315                 320

Leu Thr Lys Lys Pro Leu His Glu Tyr Gly Met Lys Asp Glu Glu Val
                325                 330                 335

Arg Gly Phe Ala Glu Ser Val Leu Lys Thr Gln Gln Arg Leu Leu Ala
            340                 345                 350

Asn Asn Tyr Val Glu Leu Thr Val Asp Glu Ile Glu Gly Ile Tyr Arg

```
                355                 360                 365

Arg Leu Tyr
    370

<210> SEQ ID NO 2
<211> LENGTH: 431
<212> TYPE: PRT
<213> ORGANISM: Artificial Sequence
<220> FEATURE:
<223> OTHER INFORMATION: Synthetic (cat2)

<400> SEQUENCE: 2

Met Lys Asp Val Leu Ala Glu Tyr Ala Ser Arg Ile Val Ser Ala Glu
1               5                   10                  15

Glu Ala Val Lys His Ile Lys Asn Gly Glu Arg Val Ala Leu Ser His
                20                  25                  30

Ala Ala Gly Val Pro Gln Ser Cys Val Asp Ala Leu Val Gln Gln Ala
            35                  40                  45

Asp Leu Phe Gln Asn Val Glu Ile Tyr His Met Leu Cys Leu Gly Glu
    50                  55                  60

Gly Lys Tyr Met Ala Pro Glu Met Ala Pro His Phe Arg His Ile Thr
65                  70                  75                  80

Asn Phe Val Gly Gly Asn Ser Arg Lys Ala Val Glu Glu Asn Arg Ala
                85                  90                  95

Asp Phe Ile Pro Val Phe Phe Tyr Glu Val Pro Ser Met Ile Arg Lys
            100                 105                 110

Asp Ile Leu His Ile Asp Val Ala Ile Val Gln Leu Ser Met Pro Asp
    115                 120                 125

Glu Asn Gly Tyr Cys Ser Phe Gly Val Ser Cys Asp Tyr Ser Lys Pro
130                 135                 140

Ala Ala Glu Ser Ala His Leu Val Ile Gly Glu Ile Asn Arg Gln Met
145                 150                 155                 160

Pro Tyr Val His Gly Asp Asn Leu Ile His Ile Ser Lys Leu Asp Tyr
                165                 170                 175

Ile Val Met Ala Asp Tyr Pro Ile Tyr Ser Leu Ala Lys Pro Lys Ile
            180                 185                 190

Gly Glu Val Glu Glu Ala Ile Gly Arg Asn Cys Ala Glu Leu Ile Glu
    195                 200                 205

Asp Gly Ala Thr Leu Gln Leu Gly Ile Gly Ala Ile Pro Asp Ala Ala
210                 215                 220

Leu Leu Phe Leu Lys Asp Lys Lys Asp Leu Gly Ile His Thr Glu Met
225                 230                 235                 240

Phe Ser Asp Gly Val Val Glu Leu Val Arg Ser Gly Val Ile Thr Gly
                245                 250                 255

Lys Lys Lys Thr Leu His Pro Gly Lys Met Val Ala Thr Phe Leu Met
            260                 265                 270

Gly Ser Glu Asp Val Tyr His Phe Ile Asp Lys Asn Pro Asp Val Glu
    275                 280                 285

Leu Tyr Pro Val Asp Tyr Val Asn Asp Pro Arg Val Ile Ala Gln Asn
290                 295                 300

Asp Asn Met Val Ser Ile Asn Ser Cys Ile Glu Ile Asp Leu Met Gly
305                 310                 315                 320

Gln Val Val Ser Glu Cys Ile Gly Ser Lys Gln Phe Ser Gly Thr Gly
                325                 330                 335

Gly Gln Val Asp Tyr Val Arg Gly Ala Ala Trp Ser Lys Asn Gly Lys
```

```
                340             345             350
Ser Ile Met Ala Ile Pro Ser Thr Ala Lys Asn Gly Thr Ala Ser Arg
            355                 360                 365

Ile Val Pro Ile Ile Ala Glu Gly Ala Val Thr Thr Leu Arg Asn
        370                 375                 380

Glu Val Asp Tyr Val Val Thr Glu Tyr Gly Ile Ala Gln Leu Lys Gly
385                 390                 395                 400

Lys Ser Leu Arg Gln Arg Ala Glu Ala Leu Ile Ala Ile Ala His Pro
                405                 410                 415

Asp Phe Arg Glu Glu Leu Thr Lys His Leu Arg Lys Arg Phe Gly
                420                 425                 430

<210> SEQ ID NO 3
<211> LENGTH: 858
<212> TYPE: PRT
<213> ORGANISM: Artificial Sequence
<220> FEATURE:
<223> OTHER INFORMATION: Synthetic (adhE2)

<400> SEQUENCE: 3

Met Lys Val Thr Asn Gln Lys Glu Leu Lys Gln Lys Leu Asn Glu Leu
1               5                   10                  15

Arg Glu Ala Gln Lys Lys Phe Ala Thr Tyr Thr Gln Glu Gln Val Asp
                20                  25                  30

Lys Ile Phe Lys Gln Cys Ala Ile Ala Ala Ala Lys Glu Arg Ile Asn
            35                  40                  45

Leu Ala Lys Leu Ala Val Glu Glu Thr Gly Ile Gly Leu Val Glu Asp
50                  55                  60

Lys Ile Ile Lys Asn His Phe Ala Ala Glu Tyr Ile Tyr Asn Lys Tyr
65                  70                  75                  80

Lys Asn Glu Lys Thr Cys Gly Ile Ile Asp His Asp Asp Ser Leu Gly
                85                  90                  95

Ile Thr Lys Val Ala Glu Pro Ile Gly Ile Val Ala Ala Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Phe Phe Ser Pro His Pro Arg Ala Lys Lys
130                 135                 140

Ser Thr Ile Ala Ala Ala Lys Leu Ile Leu Asp Ala Ala Val Lys Ala
145                 150                 155                 160

Gly Ala Pro Lys Asn Ile Ile Gly Trp Ile Asp Glu Pro Ser Ile Glu
                165                 170                 175

Leu Ser Gln Asp Leu Met Ser Glu Ala Asp Ile Ile Leu Ala Thr Gly
            180                 185                 190

Gly Pro Ser Met Val Lys Ala Ala Tyr Ser Ser Gly Lys Pro Ala Ile
        195                 200                 205

Gly Val Gly Ala Gly Asn Thr Pro Ala Ile Ile Asp Glu Ser Ala Asp
210                 215                 220

Ile Asp Met Ala Val Ser Ser Ile Ile Leu Ser Lys Thr Tyr Asp Asn
225                 230                 235                 240

Gly Val Ile Cys Ala Ser Glu Gln Ser Ile Leu Val Met Asn Ser Ile
                245                 250                 255

Tyr Glu Lys Val Lys Glu Glu Phe Val Lys Arg Gly Ser Tyr Ile Leu
            260                 265                 270

Asn Gln Asn Glu Ile Ala Lys Ile Lys Glu Thr Met Phe Lys Asn Gly
```

```
                275                 280                 285
Ala Ile Asn Ala Asp Ile Val Gly Lys Ser Ala Tyr Ile Ile Ala Lys
290                 295                 300

Met Ala Gly Ile Glu Val Pro Gln Thr Thr Lys Ile Leu Ile Gly Glu
305                 310                 315                 320

Val Gln Ser Val Glu Lys Ser Glu Leu Phe Ser His Glu Lys Leu Ser
                325                 330                 335

Pro Val Leu Ala Met Tyr Lys Val Lys Asp Phe Asp Glu Ala Leu Lys
                340                 345                 350

Lys Ala Gln Arg Leu Ile Glu Leu Gly Gly Ser Gly His Thr Ser Ser
                355                 360                 365

Leu Tyr Ile Asp Ser Gln Asn Asn Lys Asp Lys Val Lys Glu Phe Gly
                370                 375                 380

Leu Ala Met Lys Thr Ser Arg Thr Phe Ile Asn Met Pro Ser Ser Gln
385                 390                 395                 400

Gly Ala Ser Gly Asp Leu Tyr Asn Phe Ala Ile Ala Pro Ser Phe Thr
                405                 410                 415

Leu Gly Cys Gly Thr Trp Gly Gly Asn Ser Val Ser Gln Asn Val Glu
                420                 425                 430

Pro Lys His Leu Leu Asn Ile Lys Ser Val Ala Glu Arg Arg Glu Asn
                435                 440                 445

Met Leu Trp Phe Lys Val Pro Gln Lys Ile Tyr Phe Lys Tyr Gly Cys
450                 455                 460

Leu Arg Phe Ala Leu Lys Glu Leu Lys Asp Met Asn Lys Lys Arg Ala
465                 470                 475                 480

Phe Ile Val Thr Asp Lys Asp Leu Phe Lys Leu Gly Tyr Val Asn Lys
                485                 490                 495

Ile Thr Lys Val Leu Asp Glu Ile Asp Ile Lys Tyr Ser Ile Phe Thr
                500                 505                 510

Asp Ile Lys Ser Asp Pro Thr Ile Asp Ser Val Lys Lys Gly Ala Lys
                515                 520                 525

Glu Met Leu Asn Phe Glu Pro Asp Thr Ile Ile Ser Ile Gly Gly Gly
530                 535                 540

Ser Pro Met Asp Ala Ala Lys Val Met His Leu Leu Tyr Glu Tyr Pro
545                 550                 555                 560

Glu Ala Glu Ile Glu Asn Leu Ala Ile Asn Phe Met Asp Ile Arg Lys
                565                 570                 575

Arg Ile Cys Asn Phe Pro Lys Leu Gly Thr Lys Ala Ile Ser Val Ala
                580                 585                 590

Ile Pro Thr Thr Ala Gly Thr Gly Ser Glu Ala Thr Pro Phe Ala Val
                595                 600                 605

Ile Thr Asn Asp Glu Thr Gly Met Lys Tyr Pro Leu Thr Ser Tyr Glu
                610                 615                 620

Leu Thr Pro Asn Met Ala Ile Ile Asp Thr Glu Leu Met Leu Asn Met
625                 630                 635                 640

Pro Arg Lys Leu Thr Ala Ala Thr Gly Ile Asp Ala Leu Val His Ala
                645                 650                 655

Ile Glu Ala Tyr Val Ser Val Met Ala Thr Asp Tyr Thr Asp Glu Leu
                660                 665                 670

Ala Leu Arg Ala Ile Lys Met Ile Phe Lys Tyr Leu Pro Arg Ala Tyr
                675                 680                 685

Lys Asn Gly Thr Asn Asp Ile Glu Ala Arg Glu Lys Met Ala His Ala
                690                 695                 700
```

```
Ser Asn Ile Ala Gly Met Ala Phe Ala Asn Ala Phe Leu Gly Val Cys
705                 710                 715                 720

His Ser Met Ala His Lys Leu Gly Ala Met His His Val Pro His Gly
                725                 730                 735

Ile Ala Cys Ala Val Leu Ile Glu Glu Val Ile Lys Tyr Asn Ala Thr
            740                 745                 750

Asp Cys Pro Thr Lys Gln Thr Ala Phe Pro Gln Tyr Lys Ser Pro Asn
        755                 760                 765

Ala Lys Arg Lys Tyr Ala Glu Ile Ala Glu Tyr Leu Asn Leu Lys Gly
    770                 775                 780

Thr Ser Asp Thr Glu Lys Val Thr Ala Leu Ile Glu Ala Ile Ser Lys
785                 790                 795                 800

Leu Lys Ile Asp Leu Ser Ile Pro Gln Asn Ile Ser Ala Ala Gly Ile
                805                 810                 815

Asn Lys Lys Asp Phe Tyr Asn Thr Leu Asp Lys Met Ser Glu Leu Ala
            820                 825                 830

Phe Asp Asp Gln Cys Thr Thr Ala Asn Pro Arg Tyr Pro Leu Ile Ser
        835                 840                 845

Glu Leu Lys Asp Ile Tyr Ile Lys Ser Phe
    850                 855
```

<210> SEQ ID NO 4
<211> LENGTH: 314
<212> TYPE: PRT
<213> ORGANISM: Artificial Sequence
<220> FEATURE:
<223> OTHER INFORMATION: Synthetic (NCgl2810_ldhA)

<400> SEQUENCE: 4

```
Met Lys Glu Thr Val Gly Asn Lys Ile Val Leu Ile Gly Ala Gly Asp
1               5                   10                  15

Val Gly Val Ala Tyr Ala Tyr Ala Leu Ile Asn Gln Gly Met Ala Asp
            20                  25                  30

His Leu Ala Ile Ile Asp Ile Asp Glu Lys Lys Leu Glu Gly Asn Val
        35                  40                  45

Met Asp Leu Asn His Gly Val Val Trp Ala Asp Ser Arg Thr Arg Val
    50                  55                  60

Thr Lys Gly Thr Tyr Ala Asp Cys Glu Asp Ala Ala Met Val Val Ile
65                  70                  75                  80

Cys Ala Gly Ala Ala Gln Lys Pro Gly Glu Thr Arg Leu Gln Leu Val
                85                  90                  95

Asp Lys Asn Val Lys Ile Met Lys Ser Ile Val Gly Asp Val Met Asp
            100                 105                 110

Ser Gly Phe Asp Gly Ile Phe Leu Val Ala Ser Asn Pro Val Asp Ile
        115                 120                 125

Leu Thr Tyr Ala Val Trp Lys Phe Ser Gly Leu Glu Trp Asn Arg Val
    130                 135                 140

Ile Gly Ser Gly Thr Val Leu Asp Ser Ala Arg Phe Arg Tyr Met Leu
145                 150                 155                 160

Gly Glu Leu Tyr Glu Val Ala Pro Ser Ser Val His Ala Tyr Ile Ile
                165                 170                 175

Gly Glu His Gly Asp Thr Glu Leu Pro Val Leu Ser Ser Ala Thr Ile
            180                 185                 190

Ala Gly Val Ser Leu Ser Arg Met Leu Asp Lys Asp Pro Glu Leu Glu
        195                 200                 205
```

Gly Arg Leu Glu Lys Ile Phe Glu Asp Thr Arg Asp Ala Ala Tyr His
            210                 215                 220

Ile Ile Asp Ala Lys Gly Ser Thr Ser Tyr Gly Ile Gly Met Gly Leu
225                 230                 235                 240

Ala Arg Ile Thr Arg Ala Ile Leu Gln Asn Gln Asp Val Ala Val Pro
            245                 250                 255

Val Ser Ala Leu Leu His Gly Glu Tyr Gly Glu Glu Asp Ile Tyr Ile
            260                 265                 270

Gly Thr Pro Ala Val Val Asn Arg Arg Gly Ile Arg Arg Val Val Glu
            275                 280                 285

Leu Glu Ile Thr Asp His Glu Met Glu Arg Phe Lys His Ser Ala Asn
            290                 295                 300

Thr Leu Arg Glu Ile Gln Lys Gln Phe Phe
305                 310

<210> SEQ ID NO 5
<211> LENGTH: 500
<212> TYPE: PRT
<213> ORGANISM: Artificial Sequence
<220> FEATURE:
<223> OTHER INFORMATION: Synthetic (NCgl1926_mqo)

<400> SEQUENCE: 5

Met Ser Asp Ser Pro Lys Asn Ala Pro Arg Ile Thr Asp Glu Ala Asp
1               5                   10                  15

Val Val Leu Ile Gly Ala Gly Ile Met Ser Ser Thr Leu Gly Ala Met
            20                  25                  30

Leu Arg Gln Leu Glu Pro Ser Trp Thr Gln Ile Val Phe Glu Arg Leu
        35                  40                  45

Asp Gly Pro Ala Gln Glu Ser Ser Pro Trp Asn Asn Ala Gly Thr
    50                  55                  60

Gly His Ser Ala Leu Cys Glu Leu Asn Tyr Thr Pro Glu Val Lys Gly
65                  70                  75                  80

Lys Val Glu Ile Ala Lys Ala Val Gly Ile Asn Glu Lys Phe Gln Val
                85                  90                  95

Ser Arg Gln Phe Trp Ser His Leu Val Glu Glu Gly Val Leu Ser Asp
            100                 105                 110

Pro Lys Glu Phe Ile Asn Pro Val Pro His Val Ser Phe Gly Gln Gly
        115                 120                 125

Ala Asp Gln Val Ala Tyr Ile Lys Ala Arg Tyr Glu Ala Leu Lys Asp
130                 135                 140

His Pro Leu Phe Gln Gly Met Thr Tyr Ala Asp Asp Glu Ala Thr Phe
145                 150                 155                 160

Thr Glu Lys Leu Pro Leu Met Ala Lys Gly Arg Asp Phe Ser Asp Pro
                165                 170                 175

Val Ala Ile Ser Trp Ile Asp Glu Gly Thr Asp Ile Asn Tyr Gly Ala
            180                 185                 190

Gln Thr Lys Gln Tyr Leu Asp Ala Ala Glu Val Glu Gly Thr Glu Ile
        195                 200                 205

Arg Tyr Gly His Glu Val Lys Ser Ile Lys Ala Asp Gly Ala Lys Trp
    210                 215                 220

Ile Val Thr Val Lys Asn Val His Thr Gly Asp Thr Lys Thr Ile Lys
225                 230                 235                 240

Ala Asn Phe Val Phe Val Gly Ala Gly Gly Tyr Ala Leu Asp Leu Leu
                245                 250                 255

```
Arg Ser Ala Gly Ile Pro Gln Val Lys Gly Phe Ala Gly Phe Pro Val
            260                 265                 270

Ser Gly Leu Trp Leu Arg Cys Thr Asn Glu Glu Leu Ile Glu Gln His
        275                 280                 285

Ala Ala Lys Val Tyr Gly Lys Ala Ser Val Gly Ala Pro Pro Met Ser
290                 295                 300

Val Pro His Leu Asp Thr Arg Val Ile Glu Gly Lys Gly Leu Leu
305                 310                 315                 320

Phe Gly Pro Tyr Gly Gly Trp Thr Pro Lys Phe Leu Lys Glu Gly Ser
                325                 330                 335

Tyr Leu Asp Leu Phe Lys Ser Ile Arg Pro Asn Ile Pro Ser Tyr
            340                 345                 350

Leu Gly Val Ala Ala Gln Glu Phe Asp Leu Thr Lys Tyr Leu Val Thr
        355                 360                 365

Glu Val Leu Lys Asp Gln Asp Lys Arg Met Asp Ala Leu Arg Glu Tyr
    370                 375                 380

Met Pro Glu Ala Gln Asn Gly Asp Trp Glu Thr Ile Val Ala Gly Gln
385                 390                 395                 400

Arg Val Gln Val Ile Lys Pro Ala Gly Phe Pro Lys Phe Gly Ser Leu
                405                 410                 415

Glu Phe Gly Thr Thr Leu Ile Asn Asn Ser Glu Gly Thr Ile Ala Gly
            420                 425                 430

Leu Leu Gly Ala Ser Pro Gly Ala Ser Ile Ala Pro Ser Ala Met Ile
        435                 440                 445

Glu Leu Leu Glu Arg Cys Phe Gly Asp Arg Met Ile Glu Trp Gly Asp
    450                 455                 460

Lys Leu Lys Asp Met Ile Pro Ser Tyr Gly Lys Lys Leu Ala Ser Glu
465                 470                 475                 480

Pro Ala Leu Phe Glu Gln Gln Trp Ala Arg Thr Gln Lys Thr Leu Lys
                485                 490                 495

Leu Glu Glu Ala
        500

<210> SEQ ID NO 6
<211> LENGTH: 1116
<212> TYPE: DNA
<213> ORGANISM: Artificial Sequence
<220> FEATURE:
<223> OTHER INFORMATION: Synthetic (4hbD)

<400> SEQUENCE: 6
atgcagcttt tcaagctcaa gagcgtcaca catcactttg atacttttgc agagtttgcc      60
aaggaattct gtctcggtga acgcgacttg gtaattacca acgagttcat ctacgaaccg     120
tatatgaagg catgccagct gccttgtcat tttgtgatgc aggagaaata cggccaaggc     180
gagccttctg acgagatgat gaacaacatc ctagcagata ccgtaatata ccagttcgac     240
cgcgtgatcg ggatcggagg tggtacggtt attgacatct caaaactctt tgttctgaag     300
ggattaaatg atgttctcga cgcgttcgat cgcaagattc cccttatcaa agagaaagaa     360
ctgatcattg tgcccaccac ctgcggaacc ggctcggagg tgacgaacat ttccatcgcc     420
gagatcaagt cccggcacac caagatgggt ttggctgacg atgcaattgt tgctgaccac     480
gccataatca tccctgaact tctgaagagc ttgcccttcc acttctatgc atgctccgca     540
atcgatgctc ttattcatgc catcgagtca tacgtttctc aaaagcgtc tccatactcc     600
```

```
cgtctgttca gtgaggcggc gtgggacatt atcctggaag ttttcaagaa aatcgccgaa       660
cacggcccag agtaccgctt cgagaagctg ggggaaatga tcatggccag caactatgcc       720
ggtatcgctt tcggcaacgc aggcgttggc gccgtccacg ctctatccta cccgttgggc       780
ggcaactatc acgtgccgca tggagaagca aactatcagt tcttcaccga ggtctttaaa       840
gtataccaaa agaagaatcc gttcggctat attgtcgaac tcaactggaa gctctccaag       900
attctgaact gccagccaga gtacgtgtac ccgaagctgg atgaactgct cggttgcctt       960
cttaccaaga aacctttgca cgaatacggc atgaaggacg aagaggttcg tggcttcgcg      1020
gaatcggtcc tgaagaccca gcaacgcttg ctcgccaaca actacgtcga acttactgtc      1080
gatgagatcg aaggtatcta ccgacgtctc tactaa                                1116

<210> SEQ ID NO 7
<211> LENGTH: 1296
<212> TYPE: DNA
<213> ORGANISM: Artificial Sequence
<220> FEATURE:
<223> OTHER INFORMATION: Synthetic (cat2_nt)

<400> SEQUENCE: 7
atgaaggatg tactggcgga atacgcctcc cgcattgttt cggcggagga ggccgttaag        60
cacatcaaaa acgtgaacg ggtagctttg tcacacgctg ccggcgtgcc tcagagttgc       120
gttgacgcac tggtgcagca ggccgacctt ttccagaatg tggaaatcta tcacatgctg       180
tgcctcggtg agggtaagta tatggcgcct gagatggccc ctcacttccg ccacatcacc       240
aactttgtcg gtggtaactc ccgtaaggcg gtcgaagaaa accgggccga tttcattccg       300
gtattctttt acgaggtgcc aagcatgatt cgcaaagaca tcctccacat tgatgtcgcc       360
atcgttcagc tttcaatgcc tgacgaaaat ggttactgtt cctttggagt atcttgcgat       420
tactccaagc cggcagcaga gagcgctcac ctggttatcg gagaaatcaa ccgtcaaatg       480
ccatacgtac acggcgacaa cttgattcat atctccaagt ggattacat cgtgatggca        540 gactacccca tctactctct tgcaaagccc aagatcgggg aagtcgagga agctatcggg       600
aggaattgtg ccgagcttat tgaagatggt gccactctcc agctgggaat cggcgcgatt       660
cctgatgcgg ccctgttatt tctcaaggac aaaaaggatc tgggcatcca taccgaaatg       720
ttctccgatg tgttgtcga attggttcgc tccggcgtta tcacaggcaa gaaaaagact       780
cttcaccccg gaaagatggt cgcaaccttc ctgatgggaa gcgaggacgt gtatcatttc       840
atcgataaaa acccccgatgt agaactgtat ccagtagatt acgtgaatga cccgcgtgtg       900
atcgcccaaa acgacaatat ggtctcgatt aacagctgca tcgaaatcga ccttatggga       960
caggtcgtgt ccgagtgcat cggctcaaag caattcagcg gcaccggcgg ccaagttgac      1020
tacgtgcgtg gcgcagcatg gtctaaaaac ggcaaatcga tcatggcaat cccgtccact      1080
gcaaaaaacg gtacggcatc tcgaattgta cctatcatcg cggagggcgc tgctgtcacc      1140 acctgcgca acgaggtcga ttacgttgta accgagtacg gtatcgctca gctcaagggc      1200
aagagcctgc gccagcgcgc agaggctttg atcgcgatag cccacccccga cttccgtgag      1260 gaactaacga aacatctccg caagcgattc ggataa                                 1296

<210> SEQ ID NO 8
<211> LENGTH: 2577
<212> TYPE: DNA
<213> ORGANISM: Artificial Sequence
<220> FEATURE:
<223> OTHER INFORMATION: Synthetic (adhE2)
```

<400> SEQUENCE: 8

```
atgaaagtaa ccaatcagaa agagttgaag cagaagttga acgagctgcg agaggctcag    60
aagaagttcg caacctacac ccaggaacag gtggacaaga tctttaagca gtgtgccatt   120
gcagccgcga aagaacgtat taatctcgcg aaacttgcgg tcgaggaaac cggtattggg   180
ctggtagaag acaagatcat caagaaccac ttcgccgctg aatacatcta caacaagtac   240
aaaaacgaaa agacatgtgg tatcatcgac cacgacgaca gcttgggcat caccaaggta   300
gcggagccaa tcggtatcgt cgcagctatc gtgcccacta ctaaccctac ctccactgct   360
attttcaagt cactcatctc cctgaaaacc cgcaatgcta tcttcttctc acctcaccca   420
cgcgctaaga aatcaactat cgctgcagct aaacttatcc tggatgcagc cgtgaaagcc   480
ggggctccga aaacatcat cggttggatc gacgaacctt ccattgaact ctctcaagac   540
ctcatgtccg aggcagacat tatcctggca accggaggcc catccatggt taaagcagct   600
tacagctcag gcaagccggc tatcggcgtt ggagctggta acactccagc aatcatcgac   660
gagtcggccg atatcgacat ggcagtgtcc tctattatcc tgtccaaaac ttatgacaac   720
ggcgttattt gcgcgtccga gcagtctatt ctcgtcatga actctattta cgagaaggta   780
aaggaggagt ttgtgaagcg ggggtcgtac attctgaacc agaacgagat cgctaagatc   840
aaagagacta tgtttaaaaa cggagccatc aacgcagata tcgtagggaa gtccgcgtac   900
atcattgcta agatggctgg aatcgaagtc cctcaaacca cgaaaattct gatcggcgag   960
gtgcaatcgg tcgaaaagtc cgagctgttc tcgcatgaaa agttgtcccc ggtcctcgcg  1020
atgtataaag ttaaggattt tgatgaagca ctcaagaaag ctcagcgcct gatcgaattg  1080
ggtggctcgg gtcacacctc ttccctctac attgactccc agaacaataa agataaggtg  1140
aaagagttcg gcctggctat gaagacgtct cgtaccttca tcaatatgcc ctcttcacag  1200
ggcgccagcg gtgaccttta caatttcgct atcgctccta gctttaccct cggctgcggc  1260
acctggggcg gtaattctgt gtcccaaaac gtcgaaccaa agcatctgct caacattaaa  1320
agcgtcgccg aacgtcgcga gaacatgttg tggttcaagg tcccgcaaaa aatctacttc  1380
aagtatggtt gcttgcgctt tgcacttaaa gagcttaagg acatgaataa aaagcgggcg  1440
ttcatcgtca ctgataagga tctgttcaaa ctgggctatg ttaacaagat taccaaggtc  1500
ctggatgaga tcgatatcaa gtattccatc ttcaccgata ttaagtccga tccgaccatt  1560
gattccgtga agaagggcgc gaaggagatg ctcaactttg aacccgacac gattatttct  1620
attggcggag gcagcccaat ggacgcagct aaggttatgc acctgctgta tgagtaccca  1680
gaagcagaga tcgagaacct tgcaatcaat ttcatggata ttcgcaaacg catttgcaac  1740
tttcctaagc ttggtacaaa agctatctct gttgcgatcc ctaccaccgc aggaaccggc  1800
agcgaagcga caccattcgc cgttattacc aacgatgaaa caggtatgaa gtacccactt  1860
acctcttatg aacttacccc gaacatggct atcattgata cggaattgat gctgaacatg  1920
ccgcggaagt tgaccgcagc tacgggaatc gatgcattgg ttcatgcaat cgaggcatac  1980
gtttccgtca tggcaaccga ttacaccgac gagctcgcgt tgcgtgcgat taaaatgatc  2040
ttcaagtacc ttcacgcgc atacaagaat ggcacaaacg atattgaagc ccgagaaaag  2100
atggcacacg cttcgaacat cgctggtatg gccttcgcga atgcgtttct cggagtgtgt  2160
cactccatgg cgcacaaact gggagccatg catcacgtgc cccacggtat cgcatgcgcc  2220
gttcttattg aagaggtgat caagtataat gccaccgatt gccccactaa gcagacggcc  2280
```

| | |
|---|---|
| ttccctcagt acaaatcgcc caatgccaag cgtaaatacg cggaaattgc cgagtacttg | 2340 |
| aaccttaagg ggaccagcga cacggaaaag gtgaccgcac tgattgaagc catctccaag | 2400 |
| cttaagatcg acctgagcat cccacaaaac atctcagcag ccggcattaa caagaaggac | 2460 |
| ttctacaaca ctctcgacaa gatgtcgagg ctcgccttcg atgatcagtg cactaccgca | 2520 |
| aacccacgtt atccgctcat ctctgaactg aaggatatct acatcaagtc gttttaa | 2577 |

<210> SEQ ID NO 9
<211> LENGTH: 945
<212> TYPE: DNA
<213> ORGANISM: Artificial Sequence
<220> FEATURE:
<223> OTHER INFORMATION: Synthetic (NCgl2810_ldhA)

<400> SEQUENCE: 9

| | |
|---|---|
| atgaaagaaa ccgtcggtaa caagattgtc ctcattggcg caggagatgt tggagttgca | 60 |
| tacgcatacg cactgatcaa ccagggcatg gcagatcacc ttgcgatcat cgacatcgat | 120 |
| gaaaagaaac tcgaaggcaa cgtcatggac ttaaaccatg tgttgtgtg ggccgattcc | 180 |
| cgcacccgcg tcaccaaggg cacctacgct gactgcgaag acgcagccat ggttgtcatt | 240 |
| tgtgccggcg cagcccaaaa gccaggcgag acccgcctcc agctggtgga caaaaacgtc | 300 |
| aagattatga atccatcgt cggcgatgtc atggacagcg gattcgacgg catcttcctc | 360 |
| gtggcgtcca acccagtgga tatcctgacc tacgcagtgt ggaaattctc cggcttggaa | 420 |
| tggaaccgcg tgatcggctc cggaactgtc ctggactccg ctcgattccg ctacatgctg | 480 |
| ggcgaactct acgaagtggc accaagctcc gtccacgcct acatcatcgg cgaacacggc | 540 |
| gacactgaac ttccagtcct gtcctccgcg accatcgcag gcgtatcgct tagccgaatg | 600 |
| ctggacaaag cccagagct tgagggccgt ctagagaaaa ttttcgaaga cacccgcgac | 660 |
| gctgcctatc acattatcga cgccaagggc tccacttcct acggcatcgg catgggtctt | 720 |
| gctcgcatca cccgcgcaat cctgcagaac caagacgttg cagtcccagt ctctgcactg | 780 |
| ctccacggtg aatacggtga ggaagacatc tacatcggca ccccagctgt ggtgaaccgc | 840 |
| cgaggcatcc gccgcgttgt cgaactagaa atcaccgacc acgagatgga acgcttcaag | 900 |
| cattccgcaa ataccctgcg cgaaattcag aagcagttct ctaa | 945 |

<210> SEQ ID NO 10
<211> LENGTH: 1503
<212> TYPE: DNA
<213> ORGANISM: Artificial Sequence
<220> FEATURE:
<223> OTHER INFORMATION: Synthetic (NCgl1926_mqo)

<400> SEQUENCE: 10

| | |
|---|---|
| atgtcagatt cccgaagaa cgcaccgagg attaccgatg aggcagatgt agttctcatt | 60 |
| ggtgccggta tcatgagctc cacgctgggt gcaatgctgc gtcagctgga gccaagctgg | 120 |
| actcagatcg tcttcgagcg tttggatgga ccggcacaag agtcgtcctc cccgtggaac | 180 |
| aatgcaggaa ccggccactc tgctctatgc gagctgaact acaccccaga ggttaagggc | 240 |
| aaggttgaaa ttgccaaggc tgtaggaatc aacgagaagt tccaggtttc ccgtcagttc | 300 |
| tggtctcacc tcgttgaaga gggagtgctg tctgatccta aggaattcat caaccctgtt | 360 |
| cctcacgtat cttcggcca gggcgcagat caggttgcat acatcaaggc tcgctacgaa | 420 |
| gctttgaagg atcaccccact cttccagggc atgacctacg ctgacgatga agctaccttc | 480 |
| accgagaagc tgccttgat ggcaaagggc cgtgacttct ctgatccagt agcaatctct | 540 |

```
tggatcgatg aaggcaccga catcaactac ggtgctcaga ccaagcagta cctggatgca    600
gctgaagttg aaggcactga aatccgctat ggccacgaag tcaagagcat caaggctgat    660
ggcgcaaagt ggatcgtgac cgtcaagaac gtacacactg gcgacaccaa gaccatcaag    720
gcaaacttcg tgttcgtcgg cgcaggcgga tacgcactgg atctgcttcg cagcgcaggc    780
atcccacagg tcaagggctt cgctggattc ccagtatccg gcctgtggct cgttgcacc     840 aacgaggaac tgatcgagca gcacgcagcc aaggtatatg gcaaggcatc tgttggcgct    900
cctccaatgt ctgttcctca ccttgacacc cgcgttatcg agggtgaaaa gggtctgctc    960
tttggacctt acggtggctg accccctaag ttcttgaagg aaggctccta cctggacctg   1020
ttcaagtcca tccgcccaga caacattcct tcctaccttg gcgttgctgc tcaggaattt   1080
gatctgacca gtaccttgt cactgaagtt ctcaaggacc aggacaagcg tatggatgct    1140
cttcgcgagt acatgccaga ggcacaaaac ggcgattggg agaccatcgt gccggacag    1200 cgtgttcagg ttattaagcc tgcaggattc cctaagttcg gttccctgga attcggcacc   1260
accttgatca caactccga aggcaccatc gccggattgc tcggtgcttc ccctggagca    1320
tccatcgcac cttccgcaat gatcgagctg cttgagcgtt gcttcggtga ccgcatgatc   1380
gagtggggcg acaagctgaa ggacatgatc ccttcctacg caagaagct tgcttccgag    1440 ccagcactgt ttgagcagca gtgggcacgc acccagaaga ccctgaagct tgaggaagcc   1500
taa                                                                 1503

<210> SEQ ID NO 11
<211> LENGTH: 1617
<212> TYPE: DNA
<213> ORGANISM: Artificial Sequence
<220> FEATURE:
<223> OTHER INFORMATION: Synthetic (Clostridium kluyveri)

<400> SEQUENCE: 11
atgtctaaag gaatcaagaa tagccaattg aaaaaaaaga cgtcaaggc cagtaacgtt      60 gctgagaaga tcgaagagaa ggtggaaaag accgacaagg tcgttgagaa ggctgctgag    120
gtgaccgaaa agcgcattcg aaacttaaag ctccaggaaa aagttgtgac cgcagatgtc    180
gcagctgaca tgatcgagaa tggcatgatc gtcgcaatta gcggcttcac gccatccggg    240
tatccaaagg aggttccaaa agcccttact aagaaggtta atgcgctgga ggaggagttc    300
aaggtgacgc tgtataccgg ttctagcaca ggcgctgata ttgacggaga atgggcgaag    360
gcaggaataa tcgaacggcg tatcccatac cagaccaact ctgacatgag gaaaaaaata    420
aacgatggtt caatcaagta cgcagatatg cacctgagcc acatggctca atacattaac    480
tattctgtga ttcctaaggt tgacattgcc atcatcgagg cggtggccat taccgaggaa    540
ggggatatta ttcctagtac tggaatcggc aacacagcta cgtttgtcga gaatgcggat    600
aaggtaattg tggaaataaa cgaggctcag ccgcttgagt tggaaggcat ggcagatatc    660
tataccctga gaaccctcc acgtcgcgag cccatcccga tagtcaacgc aggcaaccgc    720
atagggacca cttacgtcac ctgtggctct gaaaaaatct gcgcgatcgt catgaccaac    780
acccaagaca aaacccgccc actcaccgaa gtttctcctg tcagtcaggc aatctccgat    840
aacctgattg gcttcctgaa caaagaagta gaggagggta aactcccaaa aaacctgctc    900
cccatacagt caggtgtcgg ttcggttgct aacgccgttc tagccggact ctgcgaatca    960
aacttcaaaa atttgagctg ctacacagaa gtgatccagg attcgatgtt gaagctcatc   1020
```

```
aaatgtggaa aggcagatgt ggtgtccggc acctcgatct cgccatcacc ggaaatgctg    1080
cccgagttca taaggacat  aaatttttt  cgcgaggaa  tagtactgcg cccccaggaa    1140
atatctaata atccggaaat agctcgtcgt ataggagtga tctccataaa cactgctttg    1200
gaagtagaca tctacggtaa tgtgaactcc acgcatgtca tgggctccaa gatgatgaac    1260
ggcatcggcg gcagcggcga cttcgcccgc aacgcatacc tcaccatatt cactacggag    1320
tccatcgcga agaagggcga catttcctct atcgttccta tggtttccca cgtggaccac    1380
accgagcatg acgtaatggt catcgttacc gaacagggg  ttgcggatct gcgcggtctt    1440 tccctcggg  aaaaggccgt ggcgataatt gagaattgcg tccacccgga ttacaaggat    1500
atgctcatgg agtacttcga ggaggcttgt aagtcctcag gtggcaacac cccacacaac    1560
cttgaaaaag ccctatcctg gcacactaag ttcataaaaa ctggctcgat gaagtaa      1617

<210> SEQ ID NO 12
<211> LENGTH: 1356
<212> TYPE: DNA
<213> ORGANISM: Artificial Sequence
<220> FEATURE:
<223> OTHER INFORMATION: Synthetic (Clostridium kluyveri)

<400> SEQUENCE: 12
atggaaataa aagagatggt gtcgttggca aggaaagctc agaaggaata tcaagcgacc      60
cataatcaag aagcagttga taacatttgc cgagctgcag caaagtgat  ttatgaaaat     120 gcagctatac tggctcgcga agcagtagac gaaaccggca tgggcgtata tgaacataaa     180
gtggccaaga tcaggggaa  atccaaaggc gtctggtaca atttgcacaa taaaaaatcg     240
atcggtatct taaatataga cgagagaacc gggatgatcg agatagcaaa acctatcggg     300
gttgttggag ccgtaacccc gacgacaaac ccgattgtga ctccaatgag caacatcatt     360 tttgcccctta agacatgcaa tgccattatt atcgccccac atcccagatc caaaaaatgc     420
tcagcacatg cagttcgtct gataaaggaa gcaatcgctc cgtttaatgt cccggaggga     480
atggttcaga tcattgaaga gcccagcatc gagaaaactc aggaactaat gggcgccgtg     540
gatgtggtag ttgcgacggg tggtatgggt atggtgaaat ctgcatattc ttcagggaag     600
ccttcttttg gtgtaggagc cggtaacgtt caagtgatcg tggatagtaa tatcgatttt     660
gaagctgcgg cagaaaaaat tatcaccggc cgtgctttcg acaatgggat catctgttca     720
ggcgaacaga gtatcatcta caacgaagct gacaaggaag ctgtcttcac agccttccgc     780
aaccatggtg catattttg  tgatgaagcg gaggagatc  gggcccgtgc tgcgattttt     840
gagaatggcg ccatcgcgaa agatgtagtc ggccagagcg ttgcctttat cgcgaagaaa     900
gcaaatatca atataccgga gggtacccgt attctggttg ttgaagctcg cggcgtcgga     960
gcagaggatg tcatatgtaa ggaaaaaatg tgtccagtta tgtgcgcctt aagctacaag    1020
cacttcgagg aagtgtaga  atcgcacgt  acgaacttgg ccaacgaagg taacggccat    1080
acctgtgcga tccattccaa caatcaggcg catatcatac tggcaggttc agaactgacg    1140
gtttcgcgga tcgtggtcaa tgcgccgagt gccactacag caggcggtca catccaaaat    1200
ggtctggcag tgacaaatac gctcggatgc gggagttggg gtaataactc tatctccgag    1260
aactttactt ataaacacct gttaaacatt agccgcatag cgccgcttaa ttcaagcatt    1320
cacattcctg atgacaaaga gatctgggaa ctctaa                             1356

<210> SEQ ID NO 13
<211> LENGTH: 43
```

```
<212> TYPE: DNA
<213> ORGANISM: Artificial Sequence
<220> FEATURE:
<223> OTHER INFORMATION: Synthetic (a primer set of ldhA_5'_HindIII)

<400> SEQUENCE: 13
catgattacg ccaagcttga gagcccacca cattgcgatt tcc                    43

<210> SEQ ID NO 14
<211> LENGTH: 42
<212> TYPE: DNA
<213> ORGANISM: Artificial Sequence
<220> FEATURE:
<223> OTHER INFORMATION: Synthetic (a primer of ldhA_up_3'_XhoI)

<400> SEQUENCE: 14
tcgaaactcg agtttcgatc ccacttcctg atttccctaa cc                     42

<210> SEQ ID NO 15
<211> LENGTH: 39
<212> TYPE: DNA
<213> ORGANISM: Artificial Sequence
<220> FEATURE:
<223> OTHER INFORMATION: Synthetic (a primer of ldhA_dn_5'_XhoI I)

<400> SEQUENCE: 15
tcgaaactcg agtaaatctt tggcgcctag ttggcgacg                         39

<210> SEQ ID NO 16
<211> LENGTH: 46
<212> TYPE: DNA
<213> ORGANISM: Artificial Sequence
<220> FEATURE:
<223> OTHER INFORMATION: Synthetic (a primer of ldhA_3'_EcoRI)

<400> SEQUENCE: 16
acgacggcca gtgaattcga cgacatctga gggtggataa agtggg                 46

<210> SEQ ID NO 17
<211> LENGTH: 20
<212> TYPE: DNA
<213> ORGANISM: Artificial Sequence
<220> FEATURE:
<223> OTHER INFORMATION: Synthetic (a primer of ldhA up)

<400> SEQUENCE: 17
atcgggcata attaaaggtg                                              20

<210> SEQ ID NO 18
<211> LENGTH: 22
<212> TYPE: DNA
<213> ORGANISM: Artificial Sequence
<220> FEATURE:
<223> OTHER INFORMATION: Synthetic (a primer of ldhA down)

<400> SEQUENCE: 18
gtcacctcat caagttctag aa                                           22

<210> SEQ ID NO 19
<211> LENGTH: 46
<212> TYPE: DNA
<213> ORGANISM: Artificial Sequence
<220> FEATURE:
<223> OTHER INFORMATION: Synthetic (a primer of mqo_5'_Xb)

<400> SEQUENCE: 19
```
ctgcaggtcg actctagaga agaagtagtc cgtcatgccg tgaacc                    46

<210> SEQ ID NO 20
<211> LENGTH: 32
<212> TYPE: DNA
<213> ORGANISM: Artificial Sequence
<220> FEATURE:
<223> OTHER INFORMATION: Synthetic (a primer of Dmqo_rev)

<400> SEQUENCE: 20
tagaagatta ttttgactg acgcgtgggg cg                                    32

<210> SEQ ID NO 21
<211> LENGTH: 45
<212> TYPE: DNA
<213> ORGANISM: Artificial Sequence
<220> FEATURE:
<223> OTHER INFORMATION: Synthetic (a primer of mqo_3'_B1)

<400> SEQUENCE: 21
ctcggtaccc ggggatcctc ttaaagcctg agatagcgag ttcca                     45

<210> SEQ ID NO 22
<211> LENGTH: 40
<212> TYPE: DNA
<213> ORGANISM: Artificial Sequence
<220> FEATURE:
<223> OTHER INFORMATION: Synthetic (a primer of Dmqo)

<400> SEQUENCE: 22
gtcaaaaata atcttctaac tgctttcttt aaagcacccg                           40

<210> SEQ ID NO 23
<211> LENGTH: 20
<212> TYPE: DNA
<213> ORGANISM: Artificial Sequence
<220> FEATURE:
<223> OTHER INFORMATION: Synthetic (a primer of mqo_up)

<400> SEQUENCE: 23
ttctacaggc ttgatggtgg                                                 20

<210> SEQ ID NO 24
<211> LENGTH: 19
<212> TYPE: DNA
<213> ORGANISM: Artificial Sequence
<220> FEATURE:
<223> OTHER INFORMATION: Synthetic (a primer of mqo_dn_rev)

<400> SEQUENCE: 24
atgaagctga tcgatgggt                                                  19

<210> SEQ ID NO 25
<211> LENGTH: 6702
<212> TYPE: DNA
<213> ORGANISM: Artificial Sequence
<220> FEATURE:
<223> OTHER INFORMATION: Synthetic (4G synthesis sequence: cat1, sucD,
      4hbD, and cat2)

<400> SEQUENCE: 25
tctagaatga ctattaatgt ctccgaacta cttgccaaag tccccacggg tctactgatt     60
ggtgattcct gggtggaagc atccgacggg gtactttcg atgtggaaaa cccagcgacg    120
ggtgaaacaa tcgcaacgct cgcgtctgct acttccgagg atgcactggc tgctcttgat    180

-continued

```
gctgcatgcg ctgttcaggc cgagtgggct aggatgccag cgcgcgagcg ttctaatatt      240
ttacgccgcg gttttgagct cgtagcagaa cgtgcagaag agttcgccac cctcatgacc      300
ttggaaatgg gcaagccttt ggctgaagct cgcggcgaag tcacctacgg caacgaattc      360
ctgcgctggt tctctgagga agcagttcgt ctgtatggcc gttacggaac cacaccagaa      420
ggcaacttgc ggatgctgac cgccctcaag ccagttggcc cgtgcctcct gatcacccca      480
tggaacttcc cactagcaat ggctactaga tgattttgca tctgctgcga aatctttgtt      540
tccccgctaa agttgaggac aggttgacac ggagttgact cgacgaatta ccaatgtga      600 gtaggtttgg tgcgtgagtt ggaaaaattc gccatactcg cccttgggtt ctgtcagctc      660
aagaattctt gagtgaccga tgctctgatt gacctaactg cttgacacat tgcatttcct      720
acaatcttta gaggagacac aacatgtcta aaggaatcaa gaatagccaa ttgaaaaaaa      780
agaacgtcaa ggccagtaac gttgctgaga agatcgaaga aaggtggaa aagaccgaca       840 aggtcgttga aaggctgct gaggtgaccg aaaagcgaat tcgaaactta aagctccagg        900
aaaaagttgt gaccgcagat gtcgcagctg acatgatcga gaatggcatg atcgtcgcaa       960
ttagcggctt cacgccatcc gggtatccaa aggaggttcc aaaagccctt actaagaagg     1020
ttaatgcgct ggaggaggag ttcaaggtga cgctgtatac cggttctagc acaggcgctg     1080
atattgacgg agaatgggcg aaggcaggaa taatcgaacg gcgtatccca taccagacca     1140
actctgacat gaggaaaaaa ataaacgatg gttcaatcaa gtacgcagat atgcacctga     1200
gccacatggc tcaatacatt aactattctg tgattcctaa ggttgacatt gccatcatcg     1260
aggcggtggc cattaccgag gaaggggata ttattcctag tactgaatc ggcaacacag       1320 ctacgtttgt cgagaatgcg gataaggtaa ttgtggaaat aaacgaggct cagccgcttg     1380
agttggaagg catggcagat atctataccc tgaagaaccc tccacgtcgc gagcccatcc     1440
cgatagtcaa cgcaggcaac cgcataggga ccacttacgt cacctgtggc tctgaaaaaa     1500
tctgcgcgat cgtcatgacc aacacccaag acaaaacccg cccactcacc gaagtttctc     1560
ctgtcagtca ggcaatctcc gataacctga ttggcttcct gaacaaagaa gtagaggagg     1620
gtaaactccc aaaaaacctg ctccccatac agtcaggtgt cggttcggtt gctaacgccg     1680
tgcatcccgg actctgcgaa tcaaacttca aaaatttgag ctgctacaca gaagtgatcc     1740
aggattcgat gttgaagctg atcaaatgtg gaaaggcaga tgtggtgtcc ggcacctcga     1800
tctcgccatc accggaaatg ctgcccgagt tcataaagga cataaatttt tttcgcgaga     1860
agatagtact gcgcccccag gaaatatcta ataatccgga aatagctcgt cgtataggag     1920
tgatctccat aaacactgct ttggaagtag acatctacgg taatgtgaac tccacgcatg     1980
tcatgggctc caagatgatg aacggcatcg gcggcagcgg cgactttgcc cgcaacgcat     2040
acctcaccat attcactacg gagtccatcg cgaagaaggg cgacatttcc tctatcgttc     2100
ctatggtttc ccacgtggac cacaccgagc atgacgtaat ggtcatcgtt accgaacagg     2160
gggttgcgga tctccgcggt ctttcccctc gggaaaaggc cgtggcgata attgagaatt     2220
gcgtccaccc ggattacaag gatatgctca tggagtactt cgaggaggct tgtaagtcct     2280
caggtggcaa caccccacac aaccttgaaa aagccctatc ctggcacact aagttcataa     2340
aaactggctc gatgaagtaa ttagaggaga cacaacatgg agattaaaga gatggtcagt     2400
cttgcgcgca aagctcagaa ggagtatcag gccacccata accaagaagc tgtggacaac     2460
atctgccgag ctgcagcgaa ggttatttac gaaaatgcag caattctggc ccgcgaggca     2520
gtggacgaaa ccggcatggg tgtttacgag cacaaggtgg ccaagaatca aggcaagtcc     2580
```

```
aaaggtgttt ggtacaacct gcataacaag aagtcgattg gcatcctcaa tatcgatgag    2640
cgtaccggca tgatcgagat cgcaaaacct atcggggttg taggcgccgt tacgccaacc    2700
accaacccta tcgttactcc gatgagcaac atcatctttg ctcttaagac ctgcaacgcc    2760
atcattatcg ccccacaccc gcgctccaaa aagtgctctg cccacgcagt tcggctgatc    2820
aaagaggcta tcgctccgtt caacgtgccc gaaggtatgg ttcagatcat cgaggagcct    2880
agcatcgaga agacgcagga attgatgggc gccgtagacg tggtcgttgc taccgggggc    2940
atgggcatgg tcaagtctgc ctactcctca gggaagcctt ctttcggtgt cggagccggc    3000
aatgttcagg tgatagtgga cagcaacatc gatttcgaag cggctgcaga aaagatcatc    3060
accggacgtg ccttcgacaa cggtatcatc tgctcaggcg aacagtccat catctacaac    3120
gaggctgaca aggaagcagt tttcacagca ttccgcaacc acggtgcgta cttttgcgac    3180
gaggccgagg agatcgggc tcgtgcagcg atcttcgaaa atggagccat cgcgaaagat    3240
gttgtgggcc agtccgttgc ctttattgcc aagaaggcga acattaatat ccccgagggt    3300
actcgtattc tcgtggtcga agctcgcgga gtaggcgccg aagatgtcat ctgtaaagaa    3360
aagatgtgtc cagtcatgtg cgccctctcc tacaagcact cgaagagggg ggtagagatc    3420
gcaaggacga acctcgcaaa cgaaggcaat ggccatacct gtgctatcca ctccaacaac    3480
caagcacaca tcatcttggc aggctcggag ctgaccgtgt ctcgcatcgt ggtcaacgcg    3540
ccaagtgcta ccacagcagg cggtcacatc cagaacggtc ttgccgtcac caatactcta    3600
ggctgcggct cttggggtaa caactcgatc tccgaaaact tcacttataa acacctgctc    3660
aacatttcac gcatcgcccc gttgaactcc agcattcata tcccagatga taaggaaatc    3720
tgggaactct aattagagga gacacaacat gcagcttttc aagctcaaga gcgtcacaca    3780
tcactttgat acttttgcag agtttgccaa ggaattctgt ctcggtgaac gcgacttggt    3840
aattaccaac gagttcatct acgaaccgta tatgaaggca tgccagctgc cttgtcattt    3900
tgtgatgcag gagaaatacg gccaaggcga gccttctgac gagatgatga acaacatcct    3960
agcagatatc cgtaatatcc agttcgaccg cgtgatcggg atcggaggtg gtacggttat    4020
tgacatctca aaactctttg ttctgaaggg attaaatgat gttctcgacg cgttcgatcg    4080
caagattccc cttatcaaag agaaagaact gatcattgtg cccaccacct gcggaaccgg    4140
ctcggaggtg acgaacattt ccatcgccga gatcaagtcc cggcacacca agatgggttt    4200
ggctgacgat gcaattgttg ctgaccacgc cataatcatc cctgaacttc tgaagagctt    4260
gcccttccac ttctatgcat gctccgcaat cgatgctctt attcatgcca tcgagtcata    4320
cgtttctcca aaagcgtctc catactcccg tctgttcagt gaggcggcgt gggacattat    4380
cctggaagtt ttcaagaaaa tcgccgaaca cggcccagag taccgcttcg agaagctggg    4440
ggaaatgatc atggccagca actatgccgg tatcgctttc ggcaacgcag gcgttggcgc    4500
cgtccacgct ctatcctacc cgttgggcgg caactatcac gtgccgcatg gagaagcaaa    4560
ctatcagttc ttcaccgagg tctttaaagt ataccaaaag aagaatccgt tcggctatat    4620
tgtcgaactc aactggaagc tctccaagat tctgaactgc cagccagagt acgtgtaccc    4680
gaagctggat gaactgctcg gttgccttct taccaagaaa cctttgcacg aatacggcat    4740
gaaggacgaa gaggttcgtg gcttcgcgga atcggtcctg aagacccagc aacgcttgct    4800
cgccaacaac tacgtcgaac ttactgtcga tgagatcgaa ggtatctacc gacgtctcta    4860
ctaattagag gagacacaac atgaaggatg tactggcgga atacgcctcc cgcattgttt    4920
```

```
cggcggagga ggccgttaag cacatcaaaa acggtgaacg ggtagctttg tcacacgctg    4980
ccggcgtgcc tcagagttgc gttgacgcac tggtgcagca ggccgacctt ttccagaatg    5040
tggaaatcta tcacatgctg tgcctcggtg agggtaagta tatggcgcct gagatggccc    5100
ctcacttccg ccacatcacc aactttgtcg gtggtaactc ccgtaaggcg gtcgaagaaa    5160
accgggccga tttcattccg gtattctttt acgaggtgcc aagcatgatt cgcaaagaca    5220
tcctccacat tgatgtcgcc atcgttcagc tttcaatgcc tgacgaaaat ggttactgtt    5280
cctttggagt atcttgcgat tactccaagc cggcagcaga gagcgctcac ctggttatcg    5340
gagaaatcaa ccgtcaaatg ccatacgtac acggcgacaa cttgattcat atctccaagt    5400
tggattacat cgtgatggca gactacccca tctactctct tgcaaagccc aagatcgggg    5460
aagtcgagga agctatcggg aggaattgtg ccgagcttat tgaagatggt gccactctcc    5520
agctgggaat cggcgcgatt cctgatgcgg ccctgttatt tctcaaggac aaaaaggatc    5580
tgggcatcca taccgaaatg ttctccgatg gtgttgtcga attggttcgc tccggcgtta    5640
tcacaggcaa gaaaaagact cttcaccccg gaaagatggt cgcaaccttc ctgatggaaa    5700
gcgaggacgt gtatcatttc atcgataaaa accccgatgt agaactgtat ccagtagatt    5760
acgtgaatga cccgcgtgtg atcgcccaaa acgacaatat ggtctcgatt aacagctgca    5820
tcgaaatcga ccttatggga caggtcgtgt ccgagtgcat cggctcaaag caattcagcg    5880
gcaccggcgg ccaagttgac tacgtgcgtg gcgcagcatg gtctaaaaac ggcaaatcga    5940
tcatggcaat cccgtccact gcaaaaaacg gtacggcatc tcgaattgta cctatcatcg    6000
cggagggcgc tgctgtcacc accctgcgca acgaggtcga ttacgttgta accgagtacg    6060
gtatcgctca gctcaagggc aagagcctgc gccagcgcgc agaggctttg atcgcgatag    6120
cccaccccga cttccgtgag gaactaacga aacatctccg caagcgattc ggataacata    6180
tggcggccgc aagcttgcct cgacgaaggc gtcaccgtgg gcccctggt tgaggaaaaa     6240 gcacgagaca gcgttgcatc gcttgtcgac gccgccgtcg ccgaaggtgc caccgtcctc    6300
accggcggca aggccggcac aggtgcaggc tacttctacg aaccaacggt gctcacggga    6360
gtttcaacag atgcggctat cctgaacgaa gagatcttcg gtcccgtcgc accgatcgtc    6420
accttccaaa ccgaggaaga agccctgcgt ctagccaact ccaccgaata cggactggcc    6480
tcctatgtgt tcacccagga cacctcacgt attttccgcg tctccgatgg tctcgagttc    6540
ggcctagtgg gcgtcaattc cggtgtcatc tctaacgctg ctgcaccttt tggtggcgta    6600
aaacaatccg gaatgggccg cgaaggtggt ctcgaaggaa tcgaggagta cacctccgtg    6660
cagtacatcg gtatccggga tccttacgcc ggctaggcta gc                       6702
```

<210> SEQ ID NO 26
<211> LENGTH: 36
<212> TYPE: DNA
<213> ORGANISM: Artificial Sequence
<220> FEATURE:
<223> OTHER INFORMATION: Synthetic (a primer of 0049-1)

<400> SEQUENCE: 26

```
gcaggcatgc aagcttaaag tccccacggg tctact                              36
```

<210> SEQ ID NO 27
<211> LENGTH: 36
<212> TYPE: DNA
<213> ORGANISM: Artificial Sequence
<220> FEATURE:
<223> OTHER INFORMATION: Synthetic (a primer of 0049-2 rev)

```
<400> SEQUENCE: 27
ggccagtgcc aagctttacc gatgtactgc acggag                              36

<210> SEQ ID NO 28
<211> LENGTH: 20
<212> TYPE: DNA
<213> ORGANISM: Artificial Sequence
<220> FEATURE:
<223> OTHER INFORMATION: Synthetic (a primer of ADHE2_1_F)

<400> SEQUENCE: 28
atgaaagtaa ccaatcagaa                                                20

<210> SEQ ID NO 29
<211> LENGTH: 20
<212> TYPE: DNA
<213> ORGANISM: Artificial Sequence
<220> FEATURE:
<223> OTHER INFORMATION: Synthetic (ADHE2_2260_R)

<400> SEQUENCE: 29
aatcggtggc attatacttg                                                20

<210> SEQ ID NO 30
<211> LENGTH: 987
<212> TYPE: DNA
<213> ORGANISM: Artificial Sequence
<220> FEATURE:
<223> OTHER INFORMATION: Synthetic (mdh(NCgl2297))

<400> SEQUENCE: 30
atgaattccc cgcagaacgt ctccaccaag aaggtcaccg tcaccggcgc agctggtcaa    60
atctcttatt cactgttgtg gcgcatcgcc aacggtgaag tattcggcac cgacacccct   120
gtagaactga aacttctgga gatccctcag gctcttggcg gggcagaggg tgtggctatg   180
gaacttctgg attctgcctt cccccctcct cgaaacatca ccatcaccgc ggatgccaat   240
gaggcattcg acggcgctaa tgcggcgttt ttggtcggtg cgaagcctcg cggaaaaggc   300
gaagagcgcg cagatttgct ggctaacaac ggcaagattt tcggacctca aggtaaagct   360
atcaatgaca acgccgcaga tgacattcgt gtcctagttg ttggaaaccc agcgaacacc   420
aacgcgttga ttgcttcagc tgcggcccca gatgttccag catcccgctt caacgcaatg   480
atgcgccttg atcacaaccg tgcgatctcc cagctggcca ccaagcttgg ccgtggatct   540
gcggaattta caacattgt ggtctgggga atcactccg caacccagtt cccagacatc   600
acctacgcaa ccgttggtgg agaaaaggtc actgacctgg ttgatcacga ttggtatgtg   660
gaggagttca ttcctcgcgt ggctaaccgt ggcgctgaaa tcattgaggt ccgtggaaag   720
tcttctgcag cttctgcagc atcctctgcg attgatcaca tgcgcgattg ggtacagggc   780
accgaggcgt ggtcctctgc ggcaattcct tccaccggtg catacggcat tcctgagggc   840 attttgtcg gtctgccaac cgtatcccgc aacggtgagt gggaaatcgt tgaaggcctg   900
gagatttccg atttccagcg cgcccgcatc gacgcgaatg ctcaggaatt gcaggccgag   960
cgcgaggcag tgcgcgactt gctctaa                                      987
```

MUTANT MICROORGANISM HAVING IMPROVED 1,4-BDO PRODUCTIVITY AND METHOD OF PREPARING 1,4-BDO USING THE MUTANT MICROORGANISM

CROSS-REFERENCE TO RELATED APPLICATIONS

This application claims the benefit of Korean Patent Application No. 10-2012-0082815, filed on Jul. 27, 2012, in the Korean Intellectual Property Office, the disclosure of which is incorporated herein in its entirety by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 50,161 Byte ASCII (Text) file named "712673_ST25.TXT," created on Jul. 25, 2013.

BACKGROUND

1. Field

The present disclosure relates to a recombinantly modified microorganisms to produce 1,4-BDO with high efficiency.

2. Description of the Related Art 1,4-Butanediol (1,4-BDO) is a polymer intermediate and industrial solvent with a global market of about 3 billion lb/year. 1,4-BDO is currently produced from petrochemical precursors, primarily acetylene, maleic anhydride, and propylene oxide.

1,4-BDO is used in various chemicals, i.e., polymers, solvents and fine chemical intermediates for the production of high performance polymers, solvents and fine chemicals, in the chemical industry. Since most chemicals with four carbons are currently derived and synthesized from 1,4-BDO or maleic anhydride, production costs are increasing as oil price increases, and thus development of a method supplementing and alternating the chemical production method is necessary. Therefore, a biological method using microorganisms is being suggested as an alternative to the chemical production method.

However, microorganisms do not produce only the desired metabolites, and when a particular metabolite is excessively produced, the growth of the microorganisms may be suppressed, or the microorganisms may stop producing the desired metabolite or may produce undesired products only. In order to overcome such a limitation, many studies have been carried out to develop microorganisms capable of specifically producing desired metabolites. However, designing modified microorganisms by modifying many metabolic pathways of the modified microorganisms to fit all possible number of cases would take too much time and effort.

In an embodiment of the present invention, a metabolic network model for analyzing metabolic characteristics of a microorganism is used to produce 1,4-BDO without the above-described limitations. Also, an increase in 1,4-BDO productivity is confirmed through culturing in actual microorganisms based on the results obtained from the network model.

Therefore, a method of modifying microorganisms to result in efficient 1,4-BDO productivity was confirmed, and thus limitations of the conventional methods of designing microorganisms have been overcome.

SUMMARY

The invention provides a recombinantly modified *Corynebacterium glutamicum* microorganism with improved 1,4-butanediol (1,4-BDO) productivity relative to an unmodified *Corynebacterium glutamicum* microorganism, wherein activity of an enzyme catalyzing a conversion reaction between malate and oxaloacetate is inactivated or weakened (i.e., reduced or decreased) relative to an unmodified *Corynebacterium glutamicum* microorganism.

The invention also provides a method of producing 1,4-BDO, the method comprising: culturing the recombinantly modified *Corynebacterium glutamicum* microorganism in a culture medium; and collecting 1,4-BDO from the culturing medium.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and/or other aspects will become apparent and more readily appreciated from the following description of the embodiments, taken in conjunction with the accompanying drawings in which.

DETAILED DESCRIPTION OF THE INVENTION

Figure 1:
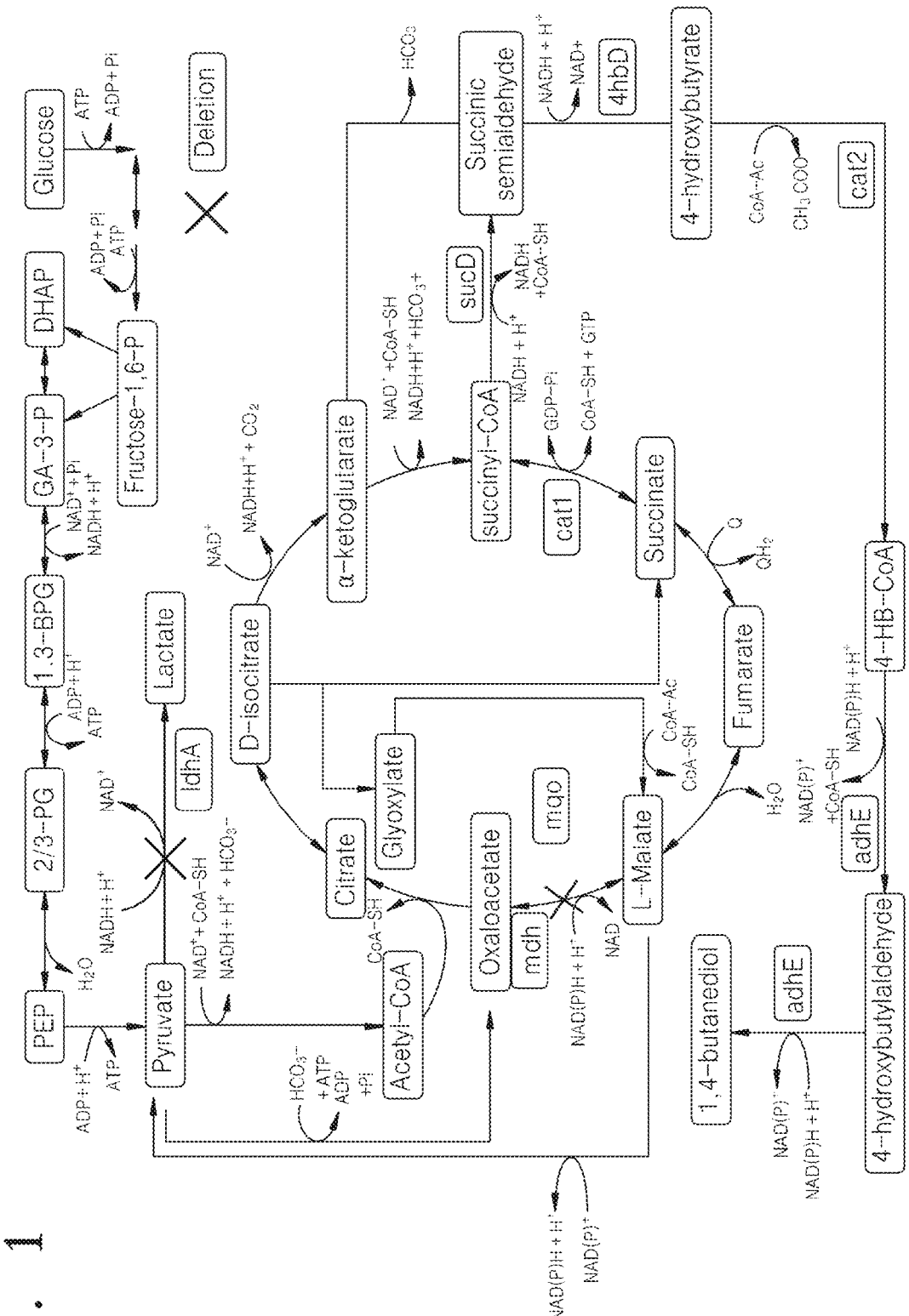
FIG. 1 illustrates biosynthetic pathways used in 1,4-BDO production, where a metabolite flux is increased in the 1,4-BDO production by deleting reactions as indicated by X (deletion).

Provided is a recombinantly modified *Corynebacterium glutamicum* producing 1,4-butanediol (BDO) obtained by modifying genes of the *Corynebacterium glutamicum*, which is a strain that does not produce 1,4-BDO.

Unless defined otherwise, all technical and scientific terms used herein have the same meaning as commonly understood by one of ordinary skill in the art to which this invention belongs. Generally, the nomenclature used herein is well known to and commonly used by those in the art.

Additional aspects will be set forth in part in the description which follows and, in part, will be apparent from the description, or may be learned by practice of the presented embodiments.

According to an aspect of the present invention, a method of predicting and obtaining metabolic pathways that enable production of an optimal metabolite by modifying a reaction network in microorganisms is provided.

In greater detail, the method of predicting the metabolic pathways that enable production of an optimal metabolite comprises, consists essentially of, or consists of (a) obtaining metabolic pathways in microorganisms and a biomass synthesis equation based on a database including information about enzymes involved in biochemical reactions in a reaction network of the microorganism; (b) using at least one of (i) information about culturing conditions of the microorganism, (ii) information about the metabolites that are produced by the microorganism, and (iii) information about the cell composition of the microorganism; (c) obtaining a primary modified metabolic pathway by introducing a biochemical reaction pathway that is not present in the microorganism; (d) obtaining a secondary modified metabolic pathway by modifying at least one of enzyme reactions involved in the primary modified metabolic pathway; (e) obtaining information of a metabolite and/or biomass produced based on the secondary modified metabolic pathway; (f) obtaining a relational equation of a metabolite-biomass based on the obtained information of the metabolite and biomass; (g) obtaining a relational equation of optimal metabolite-biomass by repeating the steps from the obtaining of the secondary modified metabolic pathway to the obtaining of the relational equation of metabolite-biomass; and (h) obtaining the secondary modified metabolic pathway that becomes basis for the relational equation of optimal metabolite-biomass.

The method of predicting the metabolic pathway is as follows.

First, the method comprises obtaining metabolic pathways in microorganisms and a biomass synthesis equation based on a database including information about enzymes involved in biochemical reactions in a reaction network of the microorganism and using at least one of (i) information conditions for culturing the microorganism, (ii) information about metabolites that are produced by the microorganism, and (iii) information about the cell composition of the microorganism.

The microorganism may be any wild-type microorganism or a modified microorganism present in the natural world. Also, the microorganisms may be bacteria, which may be *E. coli* or actinomyces. The microorganism may be preferably *Corynebacterium glutamicum*.

The term "metabolic network" is intended to mean a set of metabolic processes or physical stages determining physiological and biochemical characteristics in a cell. Also, the metabolic network includes chemical reactions of a metabolite, controlling relationships of the chemical reactions, or the like. For example, the metabolic network includes protein-protein interactions, action mechanisms of enzymes, or the like. The metabolic network may be a network of compounds and may be a network of enzymes at the same time.

The term "information about biochemical reactions" is intended to mean all information of reaction processes, which are catalyzed by particular enzymes. The information may be obtained from enzyme codes, and information of a newly found enzyme may be obtained through experiments.

The term "culturing conditions" is intended to mean conditions for culturing a microorganism. The culturing conditions may indicate, for example, carbon sources, nitrogen sources, or oxygen conditions for the microorganism to use. The carbon sources for the microorganism to use include monosaccharides, disaccharides, or polysaccharides. In particular, glucose, fructose, mannose, galactose, or the like may be used. The nitrogen sources for the microorganism to use include organic nitrogen compounds, inorganic nitrogen compounds, or the like. In particular, amino acids, amides, amines, nitrate salts, ammonium salts, or the like may be used. The oxygen conditions for culturing the microorganism include an aerobic condition of normal oxygen partial pressure, a low oxygen condition including about 0.1% to about 10% (e.g., about 0.5%, about 1%, about 2%, about 3%, about 4%, about 5%, about 6%, about 7%, about 8%, or about 9%) of oxygen in the atmosphere, or an anaerobic condition with no oxygen. The metabolic pathway may be adjusted according to the carbon sources and nitrogen sources for the microorganism to practically use.

The term "metabolite" is intended to mean any material produced by metabolic reactions of a microorganism. The metabolite may be an intermediate product of the metabolic reactions or a final product of the metabolic reactions of the microorganism. Examples of the metabolite includes succinic acid, lactic acid, 1,4-BDO (1,4-butanediol), 3-hydroxypropinate, or the like, but is not limited thereto. Preferably, the metabolite may be 1,4-BDO.

A metabolic network model for analyzing metabolic characteristics of a microorganism may be designed as follows.

First, genome information and information about each gene annotation is collected. Then, enzyme reactions of those enzymes present in *Corynebacterium glutamicum* are organized based on the genome sequence information, and a relationship between enzymes catalyzing in the enzyme reactions and genes encoding the enzymes, i.e., a GPR relationship, is organized.

The term "GPR relationship" is intended to mean a gene-protein-reaction relationship, and the GPR relationship indicates a relationship between a gene, a product of the gene, and an enzyme reaction formula that the product catalyzes.

Here, the collected gene annotation information may be directly analyzed. Also, the collected information may be used as a reference used in an amendment process followed by using the information of a metabolism-related database in which information related to the metabolic pathways is analyzed and organized.

A draft model is designed based on the GPR relationship that is organized in the manner stated above. Generally, synthesis equations of DNA replication, transcription, translation, and other parts constructing a cell (e.g., phospholipids constructing a cellular membrane, cell walls, composition of amino acid of all intracellular proteins, and overall chemical reactions of cellular polymer formation) and synthesis of a total cellular biomass are not organized in the metabolism-related database. However, the chemical reaction formulae are necessary in designing a model to mimic growth of a cell, and a composition of each component forming a cell is also necessary. The composition may be determined by performing chemical analysis on samples obtained from actual fermentation or using the information from literature.

Here, the fermentation conditions are preferred to be the same as the conditions used to ferment the sample in the actual process of model revision. The model revision process is performed on the draft model constructed in the same manner described above. The databases on metabolism contain information that is built using a bioinformatic method by analyzing gene annotation information with computer programs. Thus, such databases may possibly include imperfect or wrong metabolic information. In this regard, an error in counting the number of metabolites, maintenance energy used in life maintaining activity and growth of a cell, or the like needs to be considered in the enzyme reactions based on traits determined from actual fermentation experiments rather than only the information obtained using bioinformatic methods, and accordingly, the enzyme reactions may be revised.

In one embodiment, the metabolic network model for analyzing metabolic characteristics of the *Corynebacterium glutamicum* microorganism is the model published in Yohei Shinfuku, Natee Sorpitiporn, Masahiro Sono, Chikara Furusawa, Takashi Hirasawa and Hiroshi Shimizu, Microbial Cell Factories 209, 8:43 "Development and experimental verification of a genome scale metabolic model for *Corynebacte*-

*rium glutamicum*," and Kjeld R. Kjeldsen and Jens Nielsen, Biotechnology and Bioengineering, Vol 102, No 2, Feb. 1, 2009 "In Silico Genome-Scale Reconstruction and Validation of the *Corynebacterium glutamicum* Metabolic Network."

The candidates (I) of deletion target enzymes are determined using linear programming methods on the revised enzyme reaction chemical formulae, wherein blocking one or a combination of two enzyme reactions increases the 1,4-BDO productivity while setting the initial conditions of cell growth rate or metabolic flux as positive values.

The metabolic flux vector (vj, j-th metabolic reaction's metabolic flux) can be calculated using the mathematical expression of the metabolic network constructed being represented with stoichiometric matrix S (Sij, the time dependent stoichiometric coefficient of the i-th metabolite in the j-th reaction) which contains all the metabolites and their metabolic pathways.

Here, a time-dependent change in X, the concentration of a metabolite, may be represented by the sum of all fluxes of metabolic reactions. If the change in X is zero, i.e., a quasi-stationary state assumption, the change in X may be defined as Equation 1 below:

$$dX/dt = Sv(X;k)$$ Equation 1

(Here, Sv is a change in X, X is a concentration of a metabolite, t is time, and k is a constant.)

The metabolite fluxes in a cell may be predicted by setting a reaction to optimize, i.e., maximize or minimize, from the stoichiometry matrix S as an objective function and using a linear programming (Kim et al., Mol Biosyst. 4(2):113, 2008). In an embodiment of the present invention, a cell growth rate is optimized by setting an enzyme reaction as an objective function which illustrates compositions of a cell from the stoichiometry matrix S.

Also, the linear programming for the analysis of metabolite fluxes needs to be applied under an assumption that only the nutrition actually used in fermentation of this strain is supplied. Since quantitatively figuring each composition of a complex medium used in general is too difficult, a conventionally optimized synthetic medium is preferably used.

The term "biomass synthetic equation" is intended to mean overall metabolic reactions of a microorganism. In particular, the biomass synthetic equation represents relationships between biological components, such as proteins, nucleic acids, or lipids, and a biomass. The biomass synthetic equation may vary depending on a microorganism the equation is applied to. Moreover, initial conditions may be set to make a reaction rate of a cellular growth reaction or a metabolite flux value positive.

When a microorganism is *Corynebacterium glutamicum*, the reaction may be represented by Reaction 1 below:

0.56 PROTEIN+0.107 RNA+0.007 DNA+0.052 PHOSPHOLIPID+0.03 COF+0.110 CW+0.265 CARBOHYDRATE+70.37 ATP BIOMASS+ 70.37 ADP+70.37 Pi   Reaction 1

An algorithm suggested in the prior art (Burgard et al., Biotechnol Bioeng 84, 647-57, 2003) is modified to derive a trade-off curve representing a relationship between a metabolite and a biomass. First, an allowable range of useful product formation rates is obtained by attaining the maximum value of the useful product formation rate and the minimum value of the useful product formation rate. Next, a specific growth rate is maximized within the allowable range, and a method to derive a trade-off curve between two objective functions is used. According to the reference above, a method to find candidate genes through the trade-off curve is not precisely described. Meanwhile, an embodiment of the present invention compared productivities of a useful product of corresponding strains by examining a relationship between the production rate of a useful product in the microorganism introduced with the corresponding genes and a cellular growth rate and selecting a combination of external candidate genes, which have a curve with a slow biomass reduction despite a reduction of the production rate of a useful product.

In addition, a biochemical reaction pathway that is not present in the microorganism can be introduced so that the method according to an embodiment of the present invention may include obtaining a first modified metabolic pathway.

The term "biochemical reaction pathway" is intended to mean a set of biochemical reactions that is catalyzed by one or more specific enzymes. The biochemical reaction pathway may be catalyzed by one or more enzymes, and may be used along with a holoenzyme, coenzyme, or cofactor.

The term "first modified metabolic pathway" is intended to mean a metabolic pathway that is modified as the new biochemical reaction pathway is introduced into the original metabolic pathways of the microorganism. In particular, one or more enzymes not present in the microorganism are introduced to the microorganism, and the enzyme may use an intermediate product of the metabolic reactions or a final product of the metabolic reactions of the microorganism.

The biochemical reaction pathway that is not present in the microorganism may be a 1,4-BDO synthesis pathway. The introduction of the 1,4-BDO pathway may be achieved by introducing enzymes such as 4HbD (SEQ ID NO: 1), Cat2 (SEQ ID NO: 2), and AdhE2 (SEQ ID NO: 3).

Also, the method according to an embodiment of the present invention may include obtaining a second modified metabolic pathway by modifying at least one enzyme reaction involved in the first modified metabolic pathway.

The term "second modified metabolic pathway" is intended to mean that the at least one enzyme reaction involved in the first modified metabolic pathway is modified. The modification of the enzyme reaction may indicate enhancement of the enzyme reaction by introducing the enzyme or removal of the enzyme from the metabolic pathways.

Several to tens of enzyme reactions may be added or removed to analyze metabolic characteristics of a microorganism. The enzymes involved in the metabolic pathways of the microorganism may be LDHA (SEQ ID NO: 4) and MQO (SEQ ID NO: 5).

In one embodiment, the recombinant microorganism is *Corynebacterium glutamicum* ATCC13032/Δldh-4G-pADH1, which has been deposited on Feb. 13, 2012 in the Korean Collection for Type Cultures, Korea Research Institute of Bioscience and Biotechnology (KRIBB), 125 Gwahak-ro, Yuseong-gu, Daejeon 305-806, Republic of Korea under Accession No. KCTC 12137BP. The deposited strain has CAT1, SUCD, 4HBD, CAT2, and ADHE2.

In an embodiment of the present invention, a simulation that blocks an enzyme reaction within the metabolic network model is running a linear programming which maximizes the objective function, cellular growth rate while fixing the corresponding metabolite flux at 0 (=vj) of a specific enzyme reaction that is to be blocked among the metabolite flux vectors (v).

When, a metabolic rate of the cellular growth reaction or the metabolite flux value is set at 0 with respect to the enzyme reactions constructing the metabolic network of *Corynebacterium glutamicum*, and the simulation of linear programming maximizing the flux value of a solvent generation equation is applied while blocking the specific enzyme reaction by constructing one or a plurality of combinations of the enzyme reactions, the blocked enzyme reactions with an increased 1,4-BDO productivity compared to the case when the specific enzyme reaction is not blocked are selected as secondary deletion target candidates (II) to reflect the results of conventional experiments confirming that a solvent is actively generated at a stable stage to the model.

The deletion target candidates (I) and the secondary deletion target candidates (II) obtained in aforementioned steps are compared, and the overlapping deletion target enzyme candidates are selected as a final deletion target enzyme group, or genes encoding the overlapping deletion target enzyme candidates are selected as deletion target genes. Here, a deletion target candidate group that is most appropriate in 1,4-BDO production is combined by observing the metabolite fluxes of an overall acid generation stage and solvent generation stage via the metabolite flux analysis.

Also, the method according to an embodiment of the present invention may include obtaining information of a metabolite and/or biomass produced based on the secondary modified metabolic pathway.

Here, the metabolite may be an intermediate product or a final metabolite. In particular, the metabolite may be succinic acid, lactic acid, or 1,4-BDO. Preferably, the metabolite may be 1,4-BDO.

Moreover, the method according to an embodiment of the present invention may include obtaining a metabolite-biomass relational equation based on the obtained information of the metabolite and/or biomass.

The term "metabolite-biomass relation equations" are equations that represent relationships between the metabolites produced by the microorganism and the biomass of the microorganism. In addition, a graph illustrating the relationships is referred to as a trade-off curve graph.

An increase or decrease of the biomass and a relationship between the metabolites and the biomass may be informed through the metabolite-biomass relation equation and the trade-off curve graph. Particularly, it is confirmed that a graph of amount of 1,4-BDO production-biomass of the modified *Corynebacterium glutamicum* changes according to a type of modified gene (see FIG. 1).

Also, the method according to an embodiment of the present invention may include obtaining an optimal metabolite-biomass relational equation by repeating from the process of obtaining the secondary modified metabolic pathway to the obtaining of the metabolite-biomass relational equations.

The secondary modified metabolic pathway may be obtained by modifying an activity of various enzymes involved in the metabolic pathways in the microorganism, accordingly the optimal metabolite-biomass relational equation may be obtained, and then an equation of metabolite-biomass relation may be obtained by using the optimal equation of metabolite-biomass relation. Here, the term "optimal" is intended to indicate the situation at which the largest amount of metabolite is produced when the biomass is maintained at or increased from a certain amount.

Also, the method according to an embodiment of the present invention may include obtaining the secondary modified metabolic pathway which becomes a base of the optimal metabolite-biomass relational equation.

Moreover, an equation for obtaining the metabolite most efficiently may be obtained by obtaining the secondary modified metabolic pathway from which the optimal equation of metabolite-biomass relation may be derived. The metabolite may be 1,4-BDO.

In this regard, modification of the microorganism may be designed by predicting the metabolic pathways producing the optimal metabolite.

According to another aspect of the present invention, a modified microorganism includes a secondary modified metabolic pathway that is predicted to produce an optimal metabolite.

In an embodiment of the present invention, an activity of an enzyme catalyzing a conversion reaction between malate and oxaloacetate is inactivated or weakened (i.e., reduced, decreased, suppressed, or inhibited), and thus a microorganism with an improved 1,4-BDO productivity may be provided.

Also, the microorganism may be bacteria, which may be *E. coli* or actinomyces. The microorganism may be preferably *Corynebacterium glutamicum*.

Examples of the enzyme involved in the conversion reaction between malate and oxaloacetate may be an enzyme catalyzing a reaction converting malate to oxaloacetate and an enzyme catalyzing a reaction converting oxaloacetate to malate. Here, an activity malate quinone oxidoreductase catalyzing a reaction converting malate to oxaloacetate, may be inactivated or weakened relative to an unmodified (e.g., wild-type) microorganism. Also, an activity of malate dehydrogenase catalyzing a reaction converting oxaloacetate to malate, may be inactivated or weakened relative to an unmodified (e.g., wild-type) microorganism. Moreover, activities of malate quinone oxidoreductase and malate dehydrogenase encoding the enzyme catalyzing the conversion reaction between malate and oxaloacetate may be inactivated or weakened relative to an unmodified (e.g., wild-type) microorganism. A polynucleotide (e.g., gene or cDNA) encoding malate quinone oxidoreductase (mqo) comprises the sequence of SEQ ID NO: 10. A (e.g., gene or cDNA) encoding malate dehydrogese (mdh) comprises the sequence of SEQ ID NO: 30.

In addition, an activity of l-lactate dehydrogenase (EC.1.1.1.27) catalyzing a reaction converting pyruvate to lactate may be inactivated or weakened relative to an unmodified (e.g., wild-type) microorganism. L-lactate dehydrogenase may be ldhA comprising the sequence of SEQ ID NO: 9.

The inactivation or weakening of an enzyme's activity may be a result of a partial or full deletion of the polynucleotide (e.g., gene) encoding the enzyme, or a mutation (substitution, insertion, or addition) in the polynucleotide (e.g., gene) that results in the production of an enzyme with reduced or no activity relative to the wild-type enzyme.

Also, when a single gene knock-out simulation is performed on the 1,4-BDO production in the microorganism by using a flux balance analysis method, a reaction stage increasing the 1,4-BDO production in hypoxic culture may be investigated. With respect to *C. glutamicum*, when the conversion reaction of malate and oxaloacetate in a tricarboxylic acid (TCA) cycle is removed or weakened, an increase in the 1,4-BDO production is predicted through the investigation, and the enzyme involved in the corresponding metabolic pathway may be malate quinone oxidoreductase or malate dehydrogenase.

Although only one activity of the enzyme may be removed, it is preferable to remove all activities of all enzymes. A modification method of an enzyme activity is enabled by deletion, insertion, or substitution of a gene that encodes the enzyme. The deletion of the deletion target gene may be performed by homologous recombination, and the homologous recombination may be performed using a gene exchange vector including the deleted target gene.

According to another aspect of the present invention, a microorganism is additionally introduced with polynucleotides (e.g., genes) encoding succinyl-CoA:coenzyme A transferase, CoA-dependent succinate semialdehyde dehydrogenase, 4-hydroxybutyrate dehydrogenase, and 4-hydroxybutyryl CoA:acetyl-CoA transferase relative to an unmodified (e.g., wild-type) microorganism.

The introduction of the polynucleotides (e.g., genes) may be achieved by a vector.

The term "vector" is intended to mean a DNA product containing a DNA sequence that is operably connected to an appropriate control sequence (e.g., a promoter or other regulatory sequences), which is capable of expressing DNA in an appropriate host. The vector may be a plasmid vector, a bacteriophage vector, a cosmid vector, or a viral vector.

The polynucleotides (e.g., genes) may produce the enzyme in a plasmid phase using the vector or may produce the enzyme by being inserted in a chromosome of the host. Alternatively or additionally, the polynucleotides (e.g., genes) may be connected to an operable promoter.

In greater detail, the microorganism of which the activities of the enzyme involved in the conversion reaction between malate and oxaloacetate and the enzyme catalyzing the reaction converting pyruvate to lactate is inactivated or weakened as stated above may additionally include a polynucleotide (e.g., gene) encoding succinyl-CoA:coenzyme A transferase catalyzing a conversion of succinate to succinyl-CoA (Cat1); a polynucleotide (e.g., gene) encoding CoA-dependent succinate semialdehyde dehydrogenase catalyzing a conversion of succinyl-CoA to succinic semialdehyde (SucD); a polynucleotide (e.g., gene) encoding 4-hydroxybutyrate dehydrogenase catalyzing a conversion of succinic semialdehyde to 4-hydroxybutyrate (4HbD); and a polynucleotide (e.g., gene) encoding 4-hydroxybutyryl CoA:acetyl-CoA transferase catalyzing a conversion of 4-hydroxybutyrate to 4-hydroxybutyl-CoA (Cat2). The microorganism may further include a polynucleotide (e.g., gene) encoding alcohol dehydrogenase catalyzing a conversion of 4-hydroxybutyl-CoA to 4-hydroxybutylaldehyde (AdhE2).

Succinyl-CoA:coenzyme A transferase (Cat1; EC.2.8.3.a) catalyzes a conversion of succinate to succinyl-CoA. A polynucleotide encoding succinyl-CoA:coenzyme A transferase (cat1) may comprise the sequence of SEQ ID NO: 11.

CoA-dependent succinate semialdehyde dehydrogenase (SucD; EC.1.2.1.b) catalyzes a conversion of succinyl-CoA to succinic semialdehyde. A polynucleotide encoding CoA-dependent succinate semialdehyde dehydrogenase (sucD) may comprise the sequence of SEQ ID NO: 12.

4-hydroxybutyrate dehydrogenase (4HbD; EC.1.1.1.a) catalyzes a conversion of succinic semialdehyde to 4-hydroxybutyrate. A polynucleotide encoding 4-hydroxybutyrate dehydrogenase (4hbD) may comprise the sequence of SEQ ID NO: 6.

4-hydroxybutyryl CoA:acetyl-CoA transferase (Cat2; EC.2.8.3.a) catalyzes a conversion of 4-hydroxybutyrate to 4-hydroxybutyl-CoA. A polynucleotide encoding 4-hydroxybutyryl CoA:acetyl-CoA transferase (cat2) may comprise the sequence of SEQ ID NO: 7.

Alcohol dehydrogenase (AdhE2; EC.1.1.1.c) catalyzes a conversion of 4-hydroxybutyl-CoA to 4-hydroxybutylaldehyde. A polynucleotide encoding alcohol dehydrogenase (adhE2) may comprise the sequence of SEQ ID NO: 8.

Particularly, a microorganism with increased amounts of expression of the cat1, sucD, 4hbD, cat2, and adhE2 genes relative to an unmodified (e.g., wild-type) microorganism, is preferable, and a promoter capable of inducing strong gene expression may be used to increase expression of each gene.

According to another aspect of the present invention, a method of preparing 1,4-BDO using the modified microorganism includes culturing the modified microorganism; and collecting 1,4-BDO from the culture medium.

The carbon source for the microorganism for use in the culture medium may be monosaccharides, disaccharides, and/or polysaccharides. In particular, glucose, fructose, mannose, galactose, or the like may be used. The nitrogen source for the microorganism may be organic nitrogen compounds, inorganic nitrogen compounds, or the like. In particular, amino acids, amides, amines, nitrate salts, ammonium salts, or the like may be used. The oxygen conditions for culturing the microorganism include an aerobic condition of normal oxygen partial pressure, a low oxygen condition including about 0.1% to about 10% (e.g., about 0.5%, about 1%, about 2%, about 3%, about 4%, about 5%, about 6%, about 7%, about 8%, or about 9%) of oxygen in the atmosphere, or an anaerobic condition with no oxygen. Also, the microorganism may be cultured under an aerobic condition first and then cultured after converting the condition to a low oxygen or anaerobic condition.

EXAMPLES

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Particularly, the embodiments are merely described below to explain a method using *Corynebacterium glutamicum* as a model system, but it is obvious to one of ordinary skill in the art that the method of the present description may be applied to other microorganisms. As used herein, the term "and/or" includes any and all combinations of one or more of the associated listed items. Expressions such as "at least one of," when preceding a list of elements, modify the entire list of elements and do not modify the individual elements of the list.

Example 1

Prediction of Metabolite Flux of a Gene Deleted Strain Using Genome Scale Metabolic Network Model of *Corynebacterium glutamicum*

Enzyme reaction information of a metabolic network of *Corynebacterium glutamicum* that has been modified to produce of 1,4-butanediol (1,4-BDO) was obtained by deleting every single reaction in the metabolic network for 1,4-BDO production (see FIG. 1) one at a time. A genome-scale metabolic model for *Corynebacterium gluamicum* disclosed in Yohei Shinfuku, Natee Sorpitiporn, Masahiro Sono, Chikara Furusawa, Takashi Hirasawa and Hiroshi Shimizu, Microbial Cell Factories 209, 8:43, 2009 "Development and experimental verification of a genomescale metabolic model for *Corynebacterium glutamicum*," and Kjeld R. Kjeldsen and Jens Nielsen, Biotechnology and Bioengineering, Vol 102, No 2, Feb. 1, 2009 "In Silico Genome-Scale Reconstruction and Validation of the *Corynebacterium glutamicum* Metabolic Network", was used as a metabolic network model for analyzing metabolic characteristics of *Corynebacterium glutamicum*.

Each gene involved in every metabolic reaction defined in the model was deleted one at a time, and a simulation was performed to estimate an increase of the target material, 1,4-BDO.

Then, the 1,4-BDO productivity corresponding to each of the deleted enzyme reactions was calculated, and thus a deletion target gene operating on each of the enzyme reactions was predicted.

Additionally, a simulation deleting multi-enzyme reactions by deleting two or three enzyme reactions at a time was performed.

Also, a simulation condition of a metabolite flux for screening the effect of the deleted gene included 1) performing simulations on models of *Corynebacterium glutamicum* with an externally inserted biosynthetic pathway of 1,4-BDO production enzyme reaction and 2) performing simulations under two oxygen conditions: (1) lower than 5% and (2) 5%-10%.

Figure 2:
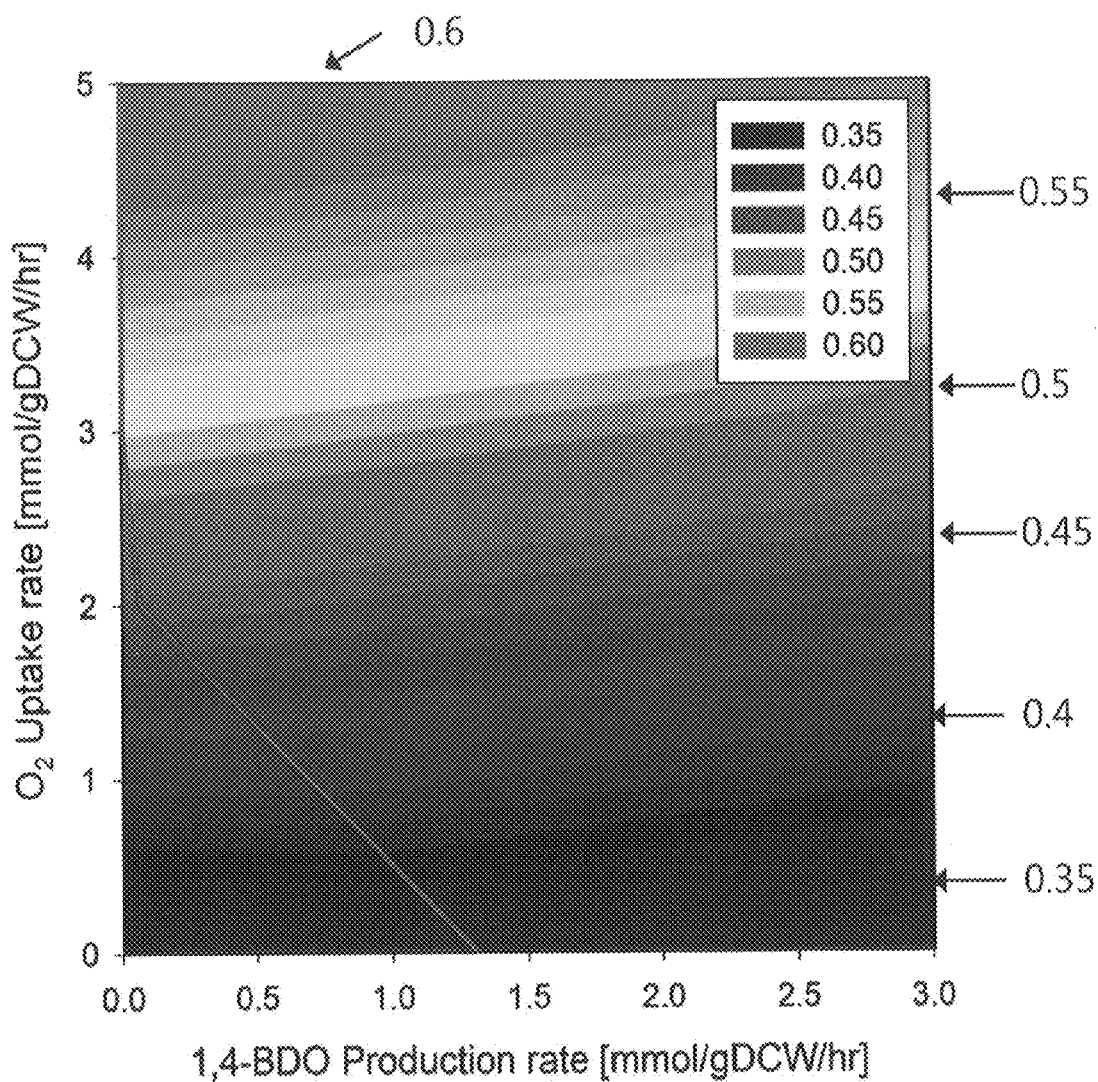
FIG. 2 illustrates oxygen uptake rate and a contour plot of biomass changing according to the 1,4-BDO production by using a genome scale metabolic modeling, where an amount of the 1,4-BDO production is predicted along the curve under biomass maximization conditions.

Next, a conventional linear programming was used to perform a method of screening the deleted genes under the aforementioned conditions. The deletion target genes obtained in such a manner were deleted from the model, and a biomass distribution of FIG. 2 was obtained while reducing an oxygen uptake rate, thus it was confirmed that a low oxygen concentration is an optimal condition for 1,4-BDO production.

Also, based on the resulting data values, a reaction between oxaloacetate and malate in a tricarboxylic acid (TCA) cycle was investigated as the deletion target enzyme reaction which may effectively produce 1,4-BDO. The gene mqo (malate quinine oxidoreductase) with a sequence of SEQ ID NO: 10 was determined to be involved in the production of 1,4-BDO.

Example 2

Preparation of Strain in which L-lactate dehydrogenase Gene is Deleted (1) Preparation of Replacement Vector L-lactate dehydrogenase (ldh) gene of *C. glutamicum* (CGL) ATCC 13032 was inactivated through a homologous recombination method by using a pK19mobsacB (ATCC 87098) vector.

Two homologous sites for deleting the ldh gene were obtained by amplifying genomic DNA of CGL ATCC 13032 as a template through PCR. The homologous sites were an upstream and a downstream of the ldh gene, each of which was obtained through PCR amplification by respectively using a primer set of ldhA_5'_HindIII (SEQ ID NO: 13) and ldhA_up_3'_XhoI (SEQ ID NO: 14) and a primer set of ldhA_dn_5'_XhoI (SEQ ID NO: 15) and ldhA_3'_EcoRI (SEQ ID NO: 16). The PCR amplification was performed by running 30 cycles of PCR, each cycle including 30 seconds of denaturation at 95° C., 30 seconds of annealing at 55° C., and 30 seconds of elongation at 72° C. Hereinafter, all PCR amplification was performed under the same conditions.

The obtained amplification product was cloned into restriction sites of restriction enzymes HindIII and EcoRI of the pK19mobsacB vector to prepare a pK19_Δldh vector.

(2) Preparation of CGL (Δldh) Strain

The pK19_Δldh vector was introduced to CGL ATCC 13032 by electroporation. The pK19_Δldh vector-introduced strain was spread on a LBHIS medium containing 25 μg/ml kanamycin and cultured at 30° C., and a colony was obtained. The LBHIS medium included 18.5 g/L brain-heart infusion broth, 0.5 M sorbitol, 5 g/L bacto-tryptone, 2.5 g/L bacto-yeast extract, 5 g/L NaCl, and 18 g/L bacto-agar. Hereinafter, a composition of a LBHIS medium is same as stated above. The obtained colony was spread on a LB-sucrose medium and cultured at 30° C., and only colonies where double crossover occurred were isolated. Genomic DNA was separated from the isolated colonies, and then ldh gene deletion was confirmed through PCR by using a primer set of ldhA up (SEQ ID NO: 17) and ldhA down (SEQ ID NO: 18).

As a result, CGL (Δldh) was obtained.

Example 3

Preparation of Strain in which Quinone Oxidoreductase Gene is Deleted (1) Preparation of Replacement Vector The malate:quinone oxidoreductase gene (mqo) of the CGL (Δldh) was inactivated through a homologous recombination method by using a pK19mobsacB (ATCC 87098) vector.

Two homologous sites for deleting the ldh gene were obtained by amplifying genomic DNA of CGL ATCC 13032 as a template through PCR. The homologous sites were an upstream site and a downstream site of the mqo gene, each of which was obtained through PCR amplification by respectively using a primer set of mqo_5'_Xb (SEQ ID NO: 19) and Dmqo_rev (SEQ ID NO: 20) and a primer set of mqo_3'_B1 (SEQ ID NO: 21) and Dmqo_for (SEQ ID NO: 22). The PCR amplification was performed by running 30 cycles of PCR, each cycle including 30 seconds of denaturation at 95° C., 30 seconds of annealing at 55° C. and 30 seconds of elongation at 72° C. Hereinafter, all PCR amplification was performed under the same conditions.

The obtained amplification product was cloned into restriction sites of restriction enzymes XbaI and BamHI of a pK19mobsacB vector to prepare a pK19_Δmqo vector.

(2) Preparation of CGL (Δldh Δmqo) Strain

The pK19_Δmqo vector was introduced to the CGL (Δldh) by electroporation. The pK19_Δmqo vector-introduced strain was spread on a LBHIS medium containing 25 μg/ml kanamycin and cultured at 30° C., and a colony was obtained. The obtained colony was spread on a LB-sucrose medium and cultured at 30° C. and only colonies where double crossover occurred were isolated. Genomic DNA was separated from the isolated colonies, and then mqo gene deletion was confirmed through PCR by using a primer set of mqo_up_for (SEQ ID NO: 23) and mqo_dn_rev (SEQ ID NO: 24).

As a result, CGL (Δldh Δmqo) was obtained.

Example 4

Preparation of Strain in which 4G Gene is Introduced (1) Preparation of pK19 gapA::4G Vector In order to insert four genes into a chromosome, a vector for inserting cat1, sucD, 4hbD, and cat2, i.e., pK19 gapA::4G, was prepared based on pK19mobsacB. The whole 4G gene comprising SEQ ID NO: 25 was synthesized and cloned into restriction sites of restriction enzymes NheI and XbaI of the pK19mobsacB vector to prepare the pK19 gapA::4G vector.

(2) Preparation of CGL (Δldh Δmqo 4G) Strain

The pK19 gapA::4G vector was introduced to the CGL (Δldh Δmqo) by electroporation. The pK19 gapA::4G vector-introduced strain was spread on a LBHIS medium containing 25 μg/ml kanamycin and cultured at 30° C., and a colony was obtained. The obtained colony was spread on a LB-sucrose medium and cultured at 30° C., and only colonies where double crossover occurred were isolated. Genomic DNA was separated from the isolated colonies, and then the 4G gene introduction was confirmed through PCR by using a primer set of 0049-1 for (SEQ ID NO: 26) and 0049-2 rev (SEQ ID NO: 27).

As a result, CGL (Δldh Δmqo 4G) was obtained.

Example 5

Preparation of Strain in Which adhE2 Gene is Introduced (1) Preparation of pK19 gapA::adhE2 Vector In order to insert adhE2 gene into a chromosome, a vector for inserting adhE2 gene, i.e., pK19 gapA::adhE2, was prepared based on pK19mobsacB. The whole adhE2 gene comprising SEQ ID NO: 8 was synthesized and cloned into sites of restriction enzymes NheI and SmaI of the pK19mobsacB vector to prepare the pK19_adhE2 vector.

(2) Preparation of CGL (Δldh Δmqo 4G adhE2) Strain

The pK19 gapA::adhE2 vector was introduced to the CGL (Δldh Δmqo 4G) by electroporation. The pK19 gapA::adhE2 vector-introduced strain was spread on a LBHIS medium containing 25 μg/ml kanamycin and cultured at 30° C., and a colony was obtained. The obtained colony was spread on a LB-sucrose medium and cultured at 30° C., and only colonies where double crossover occurred were isolated. Genomic DNA was separated from the isolated colonies, and then adhE2 gene introduction was confirmed through PCR by using a primer set of ADHE2_1_F (SEQ ID NO: 28) and ADHE2_2260_R (SEQ ID NO: 29).

As a result, CGL (Δldh Δmqo 4G adhE2) was obtained.

Example 6

Confirmation of Amount of 1,4-BDO Production

The modified *C. glutamicum* strain was used in 1,4-BDO production in a 1 L fermentor using two stages of fermentation (i.e., using conversion of an aerobic condition and an anaerobic condition). Glucose was added as a carbon source using a LPG2 medium as a base medium, and an initial glucose concentration was controlled at 50 g/L.

Figure 3:
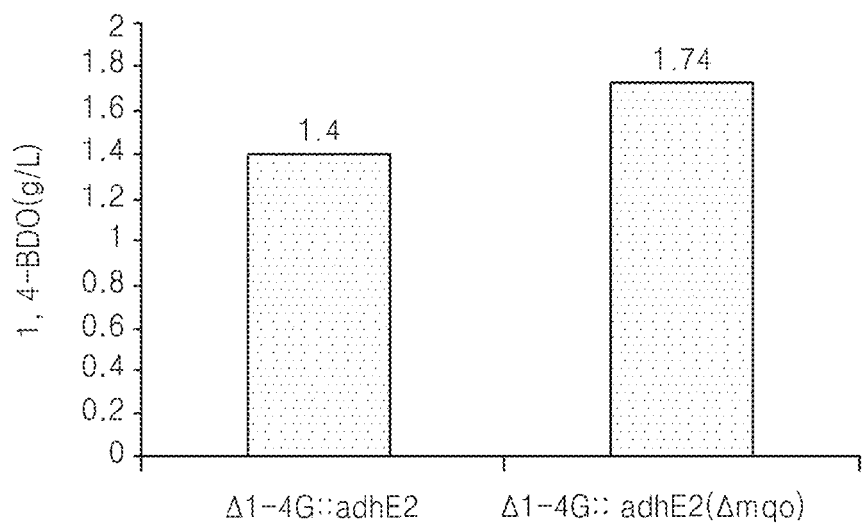
FIG. 3 is a graph that illustrates an increased amount of the 1,4-BDO production when ldh is removed and mqo is additionally removed from *Corynebacterium glutamicum* (unit: g/L).
Figure 4:
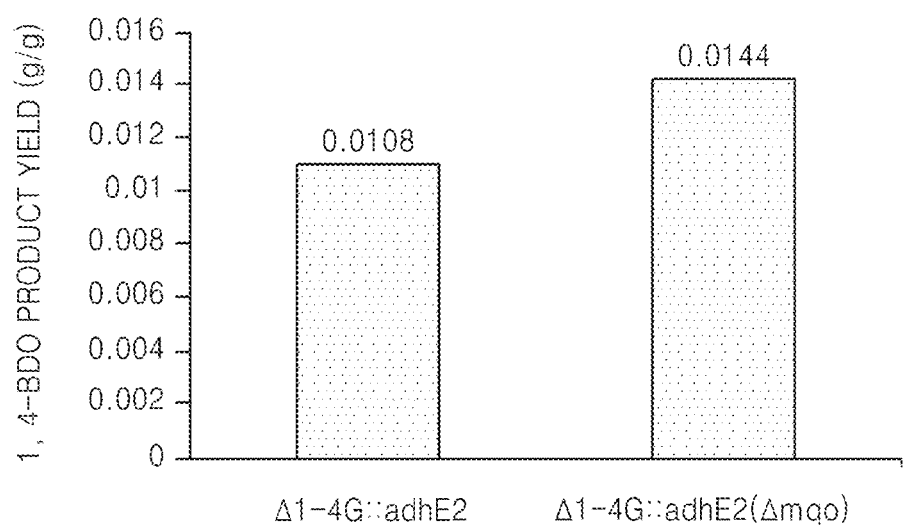
FIG. 4 is a graph that illustrates an increased product yield of 1,4-BDO when ldh is removed and mqo is additionally removed from *Corynebacterium glutamicum* (unit: %).

In the fermentation condition for a first stage of cellular growth, pH and temperature were maintained at 7.0 and 30° C., respectively. In the aerobic condition, stirring and ventilation conditions were maintained at 700 rpm and 1.5 v.v.m (volume per volume per minute), respectively. The air supply was seized during 28 hours (O.D. 65 to 70) of a period when a cell concentration entered into an initial plateau under an aerobic condition, then the stirring was reduced to 200 rpm and an anaerobic condition was applied. Under the aerobic condition, a remaining glucose concentration was maintained at about 5 g/L to about 30 g/L by intermittently adding a glucose solution with a concentration of 80% to prevent exhaustion of glucose. 20% (v/v) $NH_4OH$ was added to maintain pH of the culturing medium at 7. The fermentation proceeded up to 80 hours after conversion to the anaerobic condition, then a composition in the fermented broth was sampled and analyzed using a HPLC, and thus improvement in productivity as shown in FIG. 3 and FIG. 4 was confirmed. Productivity of 1,4-BDO increased about 20-35% relative to a control (adhE2 deletion).

As described above, according to one or more of the above embodiments of the present invention, a target enzyme or a gene thereof to increase 1,4-BDO production may be predicted by using a metabolic network model of *Corynebacterium glutamicum* according to one or more embodiments of the present invention and metabolic characteristic analysis information, such as a metabolite flux of a 1,4-BDO producing microorganism, obtained by the metabolic network model. Thus, a modified microorganism that may produce 1,4-BDO with a high efficiency may be efficiently obtained via the above stated screening.

It is the removal of the deletion target enzymes (l-lactate dehydrogenase, malate quinone oxidoreductase or malate dehydrogenase) and incorporation of genes encoding succinyl-CoA:coenzyme A transferase, CoA-dependent succinate semialdehyde dehydrogenase, 4-hydroxybutyrate dehydrogenase, 4-hydroxybutyryl CoA:acetyl-CoA transferase and optionally alcohol dehydrogenase that increases the efficiency of 1,4-BDO production. Also, the modified microorganism prepared in such a manner is capable of producing 1,4-BDO with high efficiency and thus may be effectively used for industrial purposes.

It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A recombinantly modified *Corynebacterium glutamicum* microorganism with an improved 1,4-butanediol (1,4-BDO) productivity relative to an unmodified *Corynebacterium glutamicum* microorganism, wherein malate quinone oxidoreductase activity catalyzing conversion of malate to oxaloacetate in the recombinantly modified *Corynebacterium glutamicum* microorganism is inactivated or reduced relative to an unmodified *Corynebacterium glutamicum* microorganism.

2. The recombinantly modified *Corynebacterium glutamicum* microorganism of claim 1, wherein malate dehydrogenase activity catalyzing conversion of oxaloacetate to malate in the recombinantly modified *Corynebacterium glutamicum* microorganism is inactivated or reduced relative to an unmodified *Corynebacterium glutamicum* microorganism.

3. The recombinantly modified *Corynebacterium glutamicum* microorganism of claim 1, wherein 1-lactate dehydrogenase activity catalyzing conversion of pyruvate to lactate in the recombinantly modified *Corynebacterium glutamicum* microorganism is inactivated or reduced relative to an unmodified *Corynebacterium glutamicum* microorganism.

4. The recombinantly modified *Corynebacterium glutamicum* microorganism of claim 1 comprising polynucleotides encoding succinyl-CoA:coenzyme A transferase catalyzing a conversion of succinate to succinyl-CoA; CoA-dependent succinate semialdehyde dehydrogenase catalyzing a conversion of succinyl-CoA to succinic semialdehyde; 4-hydroxybutyrate dehydrogenase catalyzing a conversion of succinic semialdehyde to 4-hydroxybutyrate; 4-hydroxybutyryl CoA:acetyl-CoA transferase catalyzing a conversion of 4-hydroxybutyrate to 4-hydroxybutyl-CoA; and alcohol dehydrogenase catalyzing a conversion of 4-hydroxybutyl-CoA to 4-hydroxybutylaldehyde.

5. The recombinantly modified *Corynebacterium glutamicum* microorganism of claim 4, wherein expression of the polynucleotides encoding succinyl-CoA:coenzyme A transferase, CoA-dependent succinate semialdehyde dehydrogenase, 4-hydroxybutyrate dehydrogenase, 4-hydroxybutyryl CoA:acetyl-CoA transferase, and alcohol dehydrogenase is increased relative to an unmodified *Corynebacterium glutamicum* microorganism.

6. The recombinantly modified *Corynebacterium glutamicum* microorganism of claim 4, wherein the polynucleotide encoding succinyl-CoA:coenzyme A transferase comprises the nucleic acid sequence of SEQ ID NO: 11, the polynucleotide encoding CoA-dependent succinate semialdehyde dehydrogenase comprises the nucleic acid sequence of SEQ ID NO: 12, the polynucleotide encoding 4-hydroxybutyrate dehydrogenase comprises the nucleic acid sequence of SEQ ID NO: 6, the polynucleotide encoding 4-hydroxybutyryl CoA:acetyl-CoA transferase comprises the nucleic acid sequence of SEQ ID NO: 7, and the polynucleotide encoding alcohol dehydrogenase comprises the nucleic acid sequence of SEQ ID NO: 8.

7. A recombinantly modified *Corynebacterium glutamicum* microorganism deposited with the Korean Collection for Type Cultures under Accession No. KCTC 12137BP.

8. A method of producing 1,4-BDO, the method comprising:

culturing the recombinantly modified microorganism of claim 1 in a culture medium; and
collecting 1,4-BDO from the culturing medium.

9. The method of claim 8, wherein the microorganism is cultured using at least one of glucose, fructose, mannose, and galactose as a carbon source.

10. The method of claim 8, wherein the microorganism is cultured under an aerobic condition, a low oxygen condition, or an anaerobic condition, wherein the low oxygen condition is less than 10% oxygen.

11. The method of claim 8, wherein the microorganism first is cultured under an aerobic condition and then is cultured under a low oxygen or anaerobic condition, wherein the low oxygen condition is less than 10% oxygen.

12. The method of claim 8, wherein the microorganism comprises malate quinone oxidoreductase with inactivated or reduced activity relative to an unmodified *Corynebacterium glutamicum* microorganism.

13. The method of claim 8, wherein the microorganism comprises malate dehydrogenase with inactivated or reduced activity relative to an unmodified *Corynebacterium glutamicum* microorganism.

14. The method of claim 8, wherein the microorganism comprises 1-lactate dehydrogenase with inactivated or reduced activity relative to an unmodified *Corynebacterium glutamicum* microorganism.

15. The method of claim 8, wherein the microorganism further comprises one or more polynucleotides encoding succinyl-CoA:coenzyme A transferase, CoA-dependent succinate semialdehyde dehydrogenase, 4-hydroxybutyrate dehydrogenase, 4-hydroxybutyryl CoA:acetyl-CoA transferase, and alcohol dehydrogenase.

16. A method of preparing a modified *Corynebacterium glutamicum* microorganism of claim 1 comprising
inactivating the expression of a gene encoding malate quinone oxidoreductase in the microorganism, or removing said gene from the microorganism.

17. The method of claim 16, further comprising introducing into the microorganism a polynucleotide encoding one or more of succinyl-CoA:coenzyme A transferase, CoA-dependent succinate semialdehyde dehydrogenase, 4-hydroxybutyrate dehydrogenase, 4-hydroxybutyryl CoA:acetyl-CoA transferase, and alcohol dehydrogenase.

18. The method of claim 17, wherein the polynucleotide comprises one or more of the nucleic acid sequences of SEQ ID NO: 6, SEQ ID NO: 7, SEQ ID NO: 8, SEQ ID NO: 11, and SEQ ID NO: 12.

19. The method of claim 16, further comprising inactivating the expression of one or more genes encoding 1-lactate dehydrogenase or malate dehydrogenase in the microorganism, or removing one or more such genes from the microorganism.

* * * * *